United States Patent
Ward et al.

(10) Patent No.: US 6,686,157 B2
(45) Date of Patent: Feb. 3, 2004

(54) SIGNAL AMPLIFICATION WITH LOLLIPOP PROBES

(75) Inventors: David C. Ward, Madison, CT (US); Patricia Bray-Ward, Madison, CT (US); Michael J. Lane, Baldwinsville, NY (US); Gyanendra Kumar, Guilford, CT (US)

(73) Assignee: Molecular Staging Inc., New Haven, CT (US)

( * ) Notice: Subject to any disclaimer, the term of this patent is extended or adjusted under 35 U.S.C. 154(b) by 0 days.

(21) Appl. No.: 09/897,259

(22) Filed: Jul. 2, 2001

(65) Prior Publication Data

US 2002/0192658 A1 Dec. 19, 2002

Related U.S. Application Data

(60) Provisional application No. 60/215,639, filed on Jun. 30, 2000.

(51) Int. Cl.[7] ............................ C12Q 1/68; C12P 19/34; C12N 9/00; C07H 21/04
(52) U.S. Cl. ......................... 435/6; 435/91.2; 435/183; 536/23.1
(58) Field of Search ....................... 435/6, 91.2, 183; 536/23.1

(56) References Cited

U.S. PATENT DOCUMENTS

| | | |
|---|---|---|
| 4,748,111 A | 5/1988 | Dattagupta et al. |
| 4,883,750 A | 11/1989 | Whiteley et al. |
| 4,965,188 A | 10/1990 | Mullis et al. |
| 4,994,373 A | 2/1991 | Stavrianopoulos et al. |
| 5,001,050 A | 3/1991 | Blanco et al. |
| 5,130,238 A | 7/1992 | Malek et al. |
| 5,198,543 A | 3/1993 | Blanco et al. |
| 5,242,794 A | 9/1993 | Whiteley et al. |
| 5,273,638 A | 12/1993 | Kenrad et al. |
| 5,328,824 A | 7/1994 | Ward et al. |
| 5,334,711 A | 8/1994 | Sproat et al. |

(List continued on next page.)

FOREIGN PATENT DOCUMENTS

| | | |
|---|---|---|
| EP | 0128332 B1 | 12/1984 |
| EP | 0356021 A2 | 2/1990 |
| EP | 0439182 B1 | 7/1991 |
| EP | 0505012 A2 | 9/1992 |
| EP | 0667393 A2 | 8/1995 |

(List continued on next page.)

OTHER PUBLICATIONS

Abravaya et al., "Detection of point mutations with a modified ligase chain reaction (Gap–LCR)," *Nucleic Acids Res.*, 23(4): 675–682 (1995).

Aliotta, J.M. et al., "Thermostable Bst DNA polymerase lacks a 3'–5' proofreading exonuclease activity," *Genet. Anal.*, 12: 185–195 (1996).

Alves and Carr, "Dot blot detection of point mutations with adjacently hybridising synthetic oligonucleotide probes," *Nucleic Acids Res.*, 16(17):8723 (1988).

(List continued on next page.)

*Primary Examiner*—Jeffrey Siew
*Assistant Examiner*—Joyce Tung
(74) *Attorney, Agent, or Firm*—Needle & Rosenberg, P.C.

(57) ABSTRACT

Disclosed is a method and compositions for the sensitive detection of the amount and location of specific nucleic acid sequences. The method makes use of a branched oligomer, referred to as a lollipop oligomer, that has a tail portion, a right arm portion, and a left arm portion. These three components are joined at a common junction making a three-tailed structure. The two arms each end with sequences complementary to adjacent sequences in a target sequence. This allows the right and left arms to be ligated together when the oligomer is hybridized to the target sequence, thus topologically linking the oligomer to the target sequence. The tail portion can then be detected at the location of the target sequence.

30 Claims, 9 Drawing Sheets

U.S. PATENT DOCUMENTS

| | | |
|---|---|---|
| 5,354,668 A | 10/1994 | Auerbach |
| 5,409,818 A | 4/1995 | Davey et al. |
| 5,427,930 A | 6/1995 | Birkenmeyer et al. |
| 5,429,807 A | 7/1995 | Matson et al. |
| 5,455,166 A | 10/1995 | Walker |
| 5,521,065 A | 5/1996 | Whiteley et al. |
| 5,591,609 A | 1/1997 | Auerbach |
| 5,599,695 A | 2/1997 | Pease et al. |
| 5,614,389 A | 3/1997 | Auerbach |
| 5,629,158 A | 5/1997 | Uhlen |
| 5,654,413 A | 8/1997 | Brenner |
| 5,714,320 A | 2/1998 | Kool |
| 5,733,733 A | 3/1998 | Auerbach |
| 5,854,033 A | 12/1998 | Lizardi |
| 5,866,336 A | 2/1999 | Nazarenko et al. |
| 5,871,928 A | 2/1999 | Fodor et al. |
| 5,876,924 A | 3/1999 | Zhang et al. |
| 5,942,391 A | 8/1999 | Zhang et al. |
| 6,033,881 A | 3/2000 | Himmler et al. |
| 6,096,880 A | 8/2000 | Kool et al. |
| 6,117,635 A | 9/2000 | Nazarenko et al. |
| 6,143,495 A | 11/2000 | Lizardi et al. |
| 6,183,960 B1 | 2/2001 | Lizardi |
| 6,210,884 B1 | 4/2001 | Lizardi |
| 6,221,603 B1 | 4/2001 | Mahtani et al. |
| 6,255,082 B1 | 7/2001 | Lizardi et al. |
| 6,291,187 B1 | 9/2001 | Kingsmore et al. |
| 6,323,009 B1 | 11/2001 | Lasken et al. |
| 6,329,150 B1 | 12/2001 | Lizardi et al. |
| 6,344,329 B1 | 2/2002 | Lizardi |

FOREIGN PATENT DOCUMENTS

| | | |
|---|---|---|
| EP | 0 745 690 A2 | 12/1996 |
| JP | 4-304900 | 10/1992 |
| JP | 4-262799 | 9/1999 |
| RU | 84173/91 | 5/1994 |
| WO | WO 91/08307 | 6/1991 |
| WO | WO 92/01813 | 2/1992 |
| WO | WO 94/24312 | 10/1994 |
| WO | WO 95/03432 | 2/1995 |
| WO | WO 95/22623 | 8/1995 |
| WO | WO 95/35390 | 12/1995 |
| WO | WO 97/19193 | 5/1997 |
| WO | WO 97/20948 | 6/1997 |
| WO | WO 97/42346 | 11/1997 |
| WO | WO 99/31276 | 6/1999 |
| WO | WO 00/7152 A1 | 11/2000 |

OTHER PUBLICATIONS

Arnold et al., "Assay Formats Involving Acridinium–Ester–Labeled DNA Probes," *Clin. Chem.*, 35:(8):1588–1594 (1989).

Barany, "Genetic Disease Detection and DNA Amplification Using Cloned Thermostable Ligase," *Proc. Natl. Acad. Sci. USA*, 88:189–193 (1991).

Bertina et al., "Mutation in blood coagulation factor V associated with resistance to activated protein C," *Nature*, 369:64–67 (1994).

Birkenmeyer et al., "DNA Probe Amplification Methods" *J. Virol. Meth.*, 35:117–126 (1991).

Blanco et al., "Characterization and purification of a phage φ 29–encoded DNA polymerase required for the initiation of replication," *Proc. Natl. Acad. Sci. USA* , 81:5325–5329 (1984).

Blanco et al., "Highly Efficient DNA Synthesis by the Phage φ29 DNA Polymerase," *Journal of Bio. Chem.*, 264(15):8935–8940 (1989).

Blanco et al., Terminal protein–primed DNA amplification, *Proc. Natl. Acad. Sci. USA*, 91:1298–12202 (1994).

Boehmer et al., "Herpes Simpled Virus Type 1 ICP8: Helix–Destabilizing Properties" *J. of Virology*, 67(2):711–715 (1993).

Broude et al., "Enhanced DNA sequencing by hybridization," *Proc. Natl. Acad. Sci. USA*, 91:3072–3076 (1994).

Burgess et al., "A new photolabile protecting group for nucleotides," *Am. Chem Soc.*, Abstracts vol. 221, Abstract 281 (1996).

Butler et al., "Bacteriophage SP6–specific RNA Polymerase," *J. of Bio. Chem.*, 257:5772–5778 (1982).

Chatterjee et al., "Cloning and Overexpression of the Gene Encoding Bacteriophage T5 DNA Polymerase" *Gene*, 97:13–19 (1991).

Chetverina, H., et al., "Cloning of RNA molecules in vitro," *Nucleic Acids Research*, 21:2349–2353 (1993).

Cremer et al., "Detection of chromosome aberrations in metaphase and interphase tumor cells by in situ hybridization using chromosome–specific library probes," *Hum Genet*, 80(3):235–46 (1988).

Daubendiek, S.L. et al., "Generation of Catalytic RNAs by rolling transcription of synthetic DNA nanocircles," *Nature Biotechnology*, 15:273–277 (1997).

Daubendiek, S.L., et al., "Rolling–Circle RNA Synthesis: Circular Oligonucleotides as Efficient Substrates for T7 RNA Polymerase," *J. Am. Chem. Soc.*, 117:7818–7819 (1995).

Davanloo et al., "Cloning and expression of the gene for bacteriophage T7 RNA polymerase," *Proc. Natl. Acad. Sci. USA,*, 81:2035–2039 (1984).

Dynal Technical Handbook, "Biomagnetic Techniques in Molecular Biology," Dynal A.S. (1995).

Ernst et al., "Cyanine dye labeling reagents for sulfhydryl groups," *Cytometry*, 10:3–10 (1989).

Fire et al., "Rolling Replication of Short DNA Cirlces" *Proc. Natl. Acad. Sci. USA*, 92:4641–4645 (1995).

Fu et al., "Hammerhead Ribozymes Containing Non–Nucleoside Linkers Are Active RNA Catalysts," *J. Am. Chem. Soc.*, 116:4591–4598 (1994).

Gasparro et al., "Site–specific targeting of psoralen photoadducts with a triple helix–forming oligonucleotide: characterization of psoralen monoadduct and crosslink formation," *Nucl. Acids Research*, 22(14):2845–2852 (1994).

Gerdes, M.G. et al., "Dynamic changes in the higher–level chromatin organization of specific sequences revealed by in situ hybridization in nuclear halos," *J. Cell Biol.*, 126(2):289–304 (1994).

Gunji et al., "Correlation Between the Serum Level of Hepatitis C Virus RNA and Disease Activities in Acute and Chronic Hepatitis C," *Int. J. Cancer*, 52:726–730 (1992).

Guo, Z. et al., "Enhanced discrimination of single nucleotide polymorphisms by artificial mismatch hybridization," *Nature Biotechnology*, 15:331–335 (1997).

Guo et al., "Direct Fluorescence Analysis of Genetic Polymorphisms by Hybridization with Oligonucleotide Arrays on Glass Supports" *Nucleotide Acids Res.*, 22(24:)5456–5465 (1994).

Gupta et al., "Expression of HIV–1 RNA in Plasma Correlates With the Development of Aids: A Multicenter Aids Cohort Study (MACS)," Ninth International Conference on AIDS/Fourth STD World Congress, Jun. 6–11, 1993, Berlin, Germany.

Haaf et al., "High resolution ordering of YAC contigs using extended chromatin and chromosomes," *Human Molecular Genetics*, 3(4):629–33 (1994).

Hacia, J.G. et al., "Detection of heterozygous mutations in BRCA1 using high density oligonucleotide arrays and two–color flurosecence analysis," *Nature Genetics*, 14:441–447, 1996.

Hagiwara et al., "Quantitation of hepatitis C Virus RNA in Serum of Asymptomatic Blood Donors and Pateitns with Type C Chronic Liver Disease," *Hepatology*, 17(4):545–550 (1993).

Hanvey et al., "Antisense and Antigene Properties of Peptide Nucleic Acdis," *Science*, 258:1481–1485 (1992).

Hata et al., "Structure of the Human Ornithine Transcarbamylase Gene," *J. Biochem.*, 103:302–308 (1988).

Hendrickson et al., "High sensitivity multianalyte immunoassay using covalent DNA–labeled antibodies and polymerase chain reaction," *Nucleic Acids Res.*, 23(3):522–529 (1995).

Holloway et al., "An exonuclease–amplification coupled capture technique improves detection of PCR product," *Nucleic Acids Research*, 21:3905–3906 (1993).

Hoy et al., "Bromodeoxyuridine/DNA Analysis of Replication in CHO Cells after Exposure to UV Light," *Mutation Research*, 290:217–230 (1993).

Hsuih et al., "*Quantitative Detection of HCV RNA using novel ligation–dependent polymerase chain reaction*" American Association for the Study of Liver Diseases (Chicago, IL, Nov. 3–7, 1995) (poster abstract).

Itakura et al., "Synthesis and Use of Synthetic Oligonucleotides" *Ann. Rev. Biochem.*, 53:323–356 (1984).

Jacobsen et al., "The N–Terminal Amino–Acid Squences of DNA Polymerase I from *Escherichia coli* and of the Large and the Small Fragments Obtained by a Limited Proteolysis," *Eur. J. Biochem.*, 45:623–627 (1974).

Johnstone et al., Immunochemistry in Practice (*Blackwell Scientific Publications*, Oxford England, 1987), pp. 209–216.

Jung et al., "Bacteriophage PRDI DNA polymerases: Evolution of DNA Polymerases" *Proc. Natl. Acad. Sci. USA*, 84:8287–8291 (1987).

Kaboord et al., "Accessory Proteins Function as Matchmakers in the Assembly of the T4 DNA Polymerase Holenzyme" *Curr. Biol.*, 5:149–157 (1995).

Kalin et al., "Evaluation of the Ligase Chain Reaction (LCR) for the Detection of Point Mutations" *Mutat. Res.*, 283(2):119–123 (1992).

Kaplan et al., "Rapid photolytic release of adenosine 5'–triphosphate from a protected analogue: utilization by the Na:K pump of human red blood cell ghosts," *Biochem.*, 17:1929–1935 (1978).

Kellogg et al., "TaqStart Antibody™, "Hot Start" PCR Facilitated by a Neutralizing Monoclonal Antibody Directe Against Taq DNA Polymerase," *BioTechniques*, 16(6):1134–1137 (1994).

Kerhof, "A Comparison of Substrates for Quantifying the Signal from a Nonradiolabeled DNA Probe" *Anal. Biochem.*, 205:359–364 (1992).

Khrapko et al., "Hybridization of DNA with Oligonucleotides Immobilized in Gel: A Convenient Method for Detecting Single Base Substitutions" *Mol/ Biol. (Mosk)*, (*USSR*) 25(3): 571–618 (1991).

King et al., "Bridging the Gap" *J. Biol. Chem.*, 269(18):13061–13064 (1994).

Kong et al., "Characterization of a DNA Polymerase from the Hyperthermophile Archaea *Thermococcus litoralis,*" *J. Biol. Chem.*, 268(3):1965–1975 (1993).

Kool, E.T., "Curcular Oligonucleotides: New Concepts in Oligonucleotide Design," *Annual Rev. Biomol. Struct.*, 25:1–28 (1996).

Kunkel et al., "Rapid and Efficient Site–Specific Mutagenesis without Phenotypic Selection," *Methods Enzymol.*, 154:367–382 (1987).

Lamture et al., "Direct detection of nucleic acid hybridization on the surface of a charge coupled device," *Nucleic Acids Research*, 22(11):2121–2125 (1994).

Landegren, "Molecular Mechanics of Nucleic Acid Sequence Amplification," *Trends Genetics*, 9:199–202 (1993).

Landegren et al., "A Ligase–Mediated Gene Detection Technique," *Science*, 241:1077–1080 (1988).

Langer et al., "Enzymatic Synthesis of Biotin–Labeled Polynucleotides: Novel Nucleic Acid Affinity Probes," *Proc. Natl. Acad. Sci. USA*, 78(11):6633–6637 (1981).

Lawyer et al., "High–Level Expression, Purification, and Enzymatic Characterization of Full–Length *Thermus Aquaticus* DNA Polymerase and a Truncated Form Deficient in 5' to 3' Exonuclease Activity," *PCR Methods Appl.*, 2(4):275–287 (1993).

LeFrere et al., "Towards a new predictors of AIDS progression through the quantitation of HIV–1 DNA copies by PCR in HIV–infected individuals," *British Journal of Haematology*, 82(2):467–471 (1992).

Lesnick et al., "Relative Thermodynamic Stability of DNA, RNA, and DNA: RNA Hybrid Duplexes: Relationship with Base Composition and Structure," *Biochemistry*, 34:10807–10815 (1995).

Lesinger et al., "Use of a Stilbenedicarboxamide Bridge in Stabilizing, Monitoring, and Photochemically Altering Folded Conformations of Oligonucleotides," *J. Am. Chem. Soc.*, 117:7323–7328 (1995).

Liu, D. et al., "Rolling circle DNA synthesis: Small circular oligonucleotides as efficient templates for DNA polymerases," *J. Am. Chem. Soc.*, 118:1587–1594 (1996).

Lizardi et al. "Mutation Detection and Single–Molecule Counting Using Isothermal Rolling–Circle Amlification," *Nature Genetics*, 19(3):225–232 (Jul. 1998).

Lockhart et al., "Expression monitoring by hybridization to high–density oligonucleotide arrays," *Nature Biotechnology*, 14:1675–1680 (1996).

Lu et al., "High concentration of Peripheral Blood Mononuclear Cells Harboring Infectious Virus Correlates with Rapid Progression of Human Immunodeficiency Virus Type 1–Related Diseases," *JID*, 168(5):1165–8116 (1993).

Lukyanov, C. et al., "Molecule by molecule PCR amplification of complex DNA mixtures for direct sequencing; an approach to in vitro cloning," *Nucleic Acids Research*, 24(11):2194–2195 (1996).

Luo, J. et al., "Improving the fidelity of *Thermus themophilus* DNA ligase," *Nucl. Acids Res.*, 24(14):3071–3078 (1996).

McCray et al., "A new approach to time–resolved studies of ATP–requiring biological systems: Laser flash photolysis of caged ATP," *Proc. Natl. Acad. Sci. USA*, 77(12):7237–7241 (1980).

McGraw et al., "Sequence–Dependent Oligonucleotide–Target Duplex Stabilities: Rules from Empirical Studies with a Set of Twenty–mers," *Biotechniques*, 8(6):674–678 (1990).

Marshall et al., "Detection of HCV RNA by teh Asymmetric Gap Ligase Chain Reaction," *PCR Methods and Applications*, 4:80–84 (1994).

Maskos, U. et al., "Oligonucleotide hybridizations on glass supports: a novel linker for oligonucleotides synthesized in situ," *Nucleic Acids Research*, 20(7):1679–1684 (1992).

Matsumoto et al., "Primary Structure of Bacteriophage M2 DNA Polymerase: Conserved Segments with Protein–Priming DNA Polymerases and DNA Polymerase I of *Escherichia coli*" Gene, 84(2):247–255 (1989).

Melton et al., "Efficient in vitro synthesis of biologically active RNA and RNA hybridization probes from plasmids containing a bacteriophage SP6 promoter," *Nucleic Acids Research*, 12(18):7035–7056 (1984).

Metzker et al., "Termination of DNA synthesis by novel 3'–modified deoxyribonucleoside 5'–triposphates," *Nucleic Acids Research*, 22(20):4259–4267 (1994).

Mujumdar et al., "Cyanine dye labeling reagents containing isothiocyanate groups," *Cytometry*, 10:11–19 (1989).

Moretti et al., "Enhancement of PCR Amplification Yield and Specificity Using AmpliTaq Gold™ DNA Polymerase," *Boitechniques*, 25:716–722 (1998).

Narang et al., "Chemical Synthesis of Deoxyoligonucleotides by the Modified Triester Method," *Methods Enzymol.*, 65:610–620 (1980).

Newton, C.R. et al., "Analysis of any point mutation in DNA. The amplification refractory mutation refractory mutation system (ARMS)," *Nucl. Acids Res.*, 17:2503–2516 (1989).

Nielsen et al., "Peptide nucleic acids (PHAs): Potential anti–sense and anti–gene agents," *Anti–Cancer Drug Design*, 8:53–63 (1993).

Nielsen et al., "Peptide Nucleic Acid (PNA). A NDA Mimic with a Peptide Backbone," *Bioconjug Chem.*, 5:3–7 (1994).

Nikiforov et al., "The Use of Phosphorothioate Primers and Exonuclease Hydrolysis for the Preparation of Single–stranded PCR Products and their Detection by Solid–phase Hybridization," *PCR Methods and Applications*, 3:285–291 (1994).

Nikiforov et al., "Genetic Analysis: a solid phase method for typing single nucleotide polymorphisms," *Nucleic Acids Research*, 22(20):4167–4175 (1994).

Nilsson, M. et al., "Padlock probes reveal single–nucleotide differences, parent of origin and in situ distribution of centromeric sequences in human chromosomes 13 and 21," *Nature Genet.*, 16:252–255 (1997).

Nilsson et al., "Padlock Probes: Circularizing Oligonucleotides for Localized DNA Detection," *Science*, 265:2085–2088 (1994).

Ørum et al., "Single base pair mutation analysis by PNA directe PCR clamping," *Nucleic Acids Research*, 21(23):5332–5336 (1993).

Panasenko et al., "A Simple, Three–Step Procedure for the Large Scale Purification of DNA Ligase from a Hybrid A Lysogen Construction in Vitro" J. Biol. Chem., 253(13):4590–4592 (1978).

Parra et al., "High resolution visual mapping of stretched DNA by fluorescent hybridization," *Nature Genet.*, 5:17–22 (1993).

Pease et al., "Light–Generated Oligonucleotide Arrays for Rapid DNA Sequence Analysis" *Proc. Natl. Acad. Sci. USA*, 91(11):5022–5026 (1994).

Piatak et al., "High Levels of HIV–1 in Plasma During All Stages of Infection Determined by Competitive PCR," *Science*, 259:1749–1754 (1993).

Pillai et al., "Photoremovable protecting groups in organic synthesis," *Synthesis*, 1–26 (1980).

Pokrovskaya et al., "In Vitro Transcription: Preparative RNA Yields in Analytical Scale Reactions," *Analytical Biochemistry*, 220:420–423 (1994).

Prakash, G. et al., "Structural effects in the recognition of DNA by circular oligonucleotides," *J. Amer. Chem. Soc.*, 114:3523–3527 (1992).

Prober et al., "A System for Rapid DNA Sequencing with Fluorescent Chain–Terminating Dideoxynucleotides," *Science*, 238:336–341 (1987).

Richards, B.et al., "Conditional mutator phenotypes in hMS2H2–deficient tumor cell lines," *Science*, 277:1523–1526 (1997).

Ried et al., "Simultaneous visualization of seven different DNA probes by in situ hybridization using combinatorial fluorescence and digital imaging microscopy," *Proc. Natl. Acad. Sci. USA*, 89(4):1388–1392 (1992).

Rigler et al., "Differences in the Mechanism of Stimulation of T7 DNA Polymerase by Two Binding Modes of *Escherichia coli* Single–stranded DNA–binding Protein," *J. Biol. Chem.*, 270(15):8910–8919 (1995).

Rychlik et al., "Optimizing of the Annealing Temperature for DNA Amplification in vitro", *Nucl. Acids. Res.*, 18(21):6409–6412 (1990).

Rys et al., "Preventing False Positives: Quantitative Evaluation of Three Protocols for Inactivation of Polymerase Chain Reaction Amplification Products," *Journal of Chinical Microbiology*, 31(9):2356–2360 (1993).

Saksela et al., "Human immunodeficiency virus type 1 mRNA expression in peripheral blood cells predicts disease progression independently of the numbers of CD4[+] lymphocytes," *Proc. Natl. Acad. Sci. USA*, 91(3):1104–1108 (1994).

Sambrook et al., "Molecular Cloning: A Laboratory Manual, Second Edition" (*Cold Spring Harbor Laboratory Press, Cold Spring Harbor, N.Y.*, 1989 (Chapter 5,6)).

Saris, C.J. et al., "Blotting of RNA into RNA exchange paper allowing subsequence characterization by in situ translation in addition to blot hybridization," *Nucleic Acids Res.*, 10(16):4831–4843 (1982).

Schena et al., "Quantitative Monitoring of Gene Expression Patterns with a Complementary DNA Microarray," *Science*, 270:467–470 (1995).

Schena, M. et al., "Parallel human genome analysis: Microarray–based expression monitoring of 1000 genes," *Proc. Natl. Acad. Sci. USA*, 93:10614–10619 (1996).

Schenborn et al., "A novel transcription property of SP6 and 17 RNA polymerase: dependence on template structure," *Nucleic Acids Research*, 13(17):6223–6236 (1985).

Schwarz, K., et al., "Improved yields of long PCR products using gene 32 protein," *Nucl. Acids Res.*, 18(4):1079 (1990).

Seigel et al., "A Novel DNA Helicase from Calf Thymus," *J. Biol. Chem.*, 267(19):13629–12635 (1992).

Skaliter et al., "Rolling Circle DNA Replication in vitro by a Complex of Herpes Simplex Virus Type 1–encoded Enzymes" *Proc. Natl. Acad. Sci. USA*, 91(22):10665–10669 (1994).

Speicher et al., "Karyotyping human chromosomes by combinatorial multi–fluor FISH," *Nature Genetics*, 12(4):368–375 (1996).

Stimpson et al., "Real–Time Detection of DNA Hybridization and Melting on Oligonucleotide Arrays by Using Optical Wave Guides," *Proc. Natl. Acad. Sci. USA*, 92(14):6379–6383 (1995).

Strauss et al., "Quantitative measure of calretinin and β–actin mRNAIN rat brain micropunches without prior isolation of RNA," *Mol. Brain Res.*, 20(3):229–239 (1993).

Studier et al., "Use of T7 RNA Polymerase to Direct Expression of Cloned Genes," *Methods in Enzymol.*, 185:60–89 (1990).

Syvänen et al., "Fast Qualification of nucleic acid hybrids by affinity–based hybrid collection," *Nucleic Acids Research*, 14(12):5037–5049 (1986).

Tabor et al., "Selective oxidation of the exonuclease domain of bacteriphage T7 DNA polymerase by in vitro mutagenesis," *J. Biol. Chem.*, 264:6447–6458 (1989).

Tabor et al., "Selective Oxidation of the Exonuclease Domain of Bacteriophage T7 DNA polymerase" *J. Biol. Chem.*, 262(32):15330–15333 (1987).

Thomas, D.C. et al., "Cascade rolling circle amplification, a homogeneous fluorescence detection system for DNA diagnostics," *Clin. Chem.*, 43:2219 Abs. 38 (1997).

Thorbjanardottir et al., "Sequence of the DNA Ligase–Encoding Gene from *Thermus Scotoductus* and conserved motifs in DNA Ligases," *Gene*, 151(1&2):177–180 (1995).

Tsurumi et al., "Functional Interaction between Epstein–Barr Virus DNA Polymerase Catalytic Subunit and Its Accessory Subunit In Vitro," *J. Virology*, 67(12):7648–7653 (1993).

Tyagi et al., "Molecular Beacons: Probes that Fluoesce Upon Hybridization," *Nat. Biotech.*, 14(3):303–308 (1996).

Velculescu, L., et al., "Serial Analysis of Gene Expression," *Science*, 270:484–487 (1995).

Vogelstein, B. et al., "Supercoiled Loops and Eucaryotic DNA Replication," *Cell*, 22:79–85 (1980).

Waggoner, A., "Covalent labeling of proteins and nucleic acids with fulorophores," *Meth. Enzymology*, 246:362–373 (1995).

Walker, G.T. et al., "Strand Displacement Amplification an Isothermal, in vitro DNA amplification technique," *Nucleic Acids Research*, 20(7):1691–1696 (1992).

Walter et al., "Strand displacement amplification as in vitro model for rolling–circle replication: Deletion formation and evolution during serial transfer," *Proc. Natl. Acad. Sci. USA*, 91:7937–7941 (1994).

Wansick et al. "Flourescent Labeling of Nascent RNA Reveals Transcription by RNA Polymerase II in Domains Scattered Throughout the Nucleus," *Journal of Cell Biology*, 122(2):283–293 (1993).

Wiegant et al., "High–resolution in situ hybridization using DNA halo preparations," *Hum. Mol Genet.*, 1(8):587–91 (1992).

Wiedmann et al., "Ligase Chain Reaction (LCR)—Overview and Applications," *PCR Methods and Applications*, (Cold Spring Habor Laboratory Press, Cold Spring Harbor Laboratory, NY, 1994), pp. S51–S64.

Winn–Deen et al., "Non–Radioactive Detection of Mycobacterium Tuberculosis LCR Products in a Microtitre Plate Format," *Mol and Cell Probes*, (England) 7(3):179–186 (1993).

Young et al., "Quantitative analysis of solution hybridisation," *Nucleic Acid Hybridisation: A Practical Approach* (IRL Press, 1985), pp. 47–71.

Yu et al., "Cyanine Dye dUTP Analogs for Enzymatic Labeling of DNA Probes," *Nucleic Acids Res.*, 22(15):3226–3232 (1994).

Yunis et al., "The Characterization of High–Resolution G–Banded Chromosomes of Man," *Chromosoma*, 67(4):293–307 (1978).

Zehavi et al., "Ligh sensitive glycosides. I. 6–Nioveratryl β–D–Glucopyranoside and 2–Nitrobenzyl β–D–Glucopyranoside," *J. Org. Chem.*, 37(14):2281–2288 (1972).

Zhu et al., "Purification and Characterization of PRD1 DNA Polymerase," *Biochem. Biophys. Acta.*, 1219(2):267–276 (1994).

Zijderveld et al., "Helix–Destabilizing Properties of the Adenovirus DNA–Binding Protein," *J Virology*, 68(2):1158–1164 (1994).

Baner et al. Signal Amplification of Padlock Probes by Rolling Circle Replication, *Nucleic Acids Research*, Oxford University Press, Surrey, 26(22):5073–5078 (1998).

Gusev et al. Rolling Circle Amplfiication: A New Approach to Increase Sensitivity for Immunohistochemistry and Flow Cytometry, *American Journal of Pathology*, 159(1: 63–69 (Jul. 2001).

Lizardi et al. Mutation Detection and Signle–Molecule Counting Using Isothermal Rolling–Circle Amplification; *Nature Genetics*, 19:225–232 (1998).

Mullenix et al. Allergen–specific IgE Detection on Microarrays Using Rolling Circle Amplification: Correlation with in Vitro Assays for Serum IgE, *Clinical Chemistry*, 47(10):1926–1929 (2001).

Nuovo, et al. In Situ Amplificaiton Using Universal Energy Transfer–labeled Primers, *The Journal of Histochemistry & Cytochemistry, The Histochemical Society, Inc., New York*, New York 43(3):27–279 (1999), XP008002684.

Schweitzer et al. Immunoassays with Rolling Circle DNA Amplification: A Versatile Platform for Utlrasensitive Antigen Detection, PNAS, 97(18):10113–10119 (Aug. 29, 2000).

Schweitzer et al. Multiplexed Protein Profiling on Microarrays by Rolling–Circle Amplification, *Nature Biotechnology*, 20:359–365 (Apr. 2002).

Tyagia et al. Moledular Beacons: Probes that Fluoresce upon Hybridization, *Nature Biotechnology*, 14:303–308 (March 1996), XP000196024.

SEQUENCE LISTING

```
<160> NUMBER OF SEQ ID NOS: 9

<210> SEQ ID NO 1
<211> LENGTH: 78
<212> TYPE: DNA
<213> ORGANISM: Artificial Sequence
<220> FEATURE:
<223> OTHER INFORMATION: Description of Artificial Sequence = synthetic construct

<400> SEQUENCE: 1
cgcatgtcct atcctcagct gtgatcatca gaactcacct gttagacgcc accagctcca      60
     actgtgaaga tcgcttat                                                    78

<210> SEQ ID NO 2
<211> LENGTH: 79
<212> TYPE: DNA
<213> ORGANISM: Artificial Sequence
<220> FEATURE:
<223> OTHER INFORMATION: Description of Artificial Sequence = synthetic construct

<400> SEQUENCE: 2
gtggaacgtg taatgttcat gatgaaatgt atccttgaca gcccgatgag gtccgtatcc      60
     ttgacagccg atgaggcac                                                   79

<210> SEQ ID NO 3
<211> LENGTH: 81
<212> TYPE: DNA
<213> ORGANISM: Artificial Sequence
<220> FEATURE:
<223> OTHER INFORMATION: Description of Artificial Sequence = synthetic construct

<400> SEQUENCE: 3
aagaactata ttgtctttct gagcggataa caagacacac aggatacagt atgacatgat      60
     tacgatgatt ccaccttctc c                                                81

<210> SEQ ID NO 4
<211> LENGTH: 52
<212> TYPE: DNA
<213> ORGANISM: Artificial Sequence
<220> FEATURE:
<223> OTHER INFORMATION: Description of Artificial Sequence = synthetic construct

<400> SEQUENCE: 4
aaaaaaaaaa aaaaaaaaaa aaaacgtca tcatgaacat tacacgttcc ac               52
```

```
<210> SEQ ID NO 5
<211> LENGTH: 81
<212> TYPE: DNA
<213> ORGANISM: Artificial Sequence
<220> FEATURE:
<223> OTHER INFORMATION: Description of Artificial Sequence = synthetic construct

<400> SEQUENCE: 5
aagaactata ttgtctttct gagcggataa caagacacac aggatacagt atgacatgat      60
     tacggtgatt ccaccttctc a                                                81

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence = synthetic construct

<400> SEQUENCE: 6
aaaaaaaaaa aaaaacatgt tgttacacag ctgaggatag gacat                      45

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence = synthetic construct

<400> SEQUENCE: 7
tcagaactca cctgttag                                                    18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence = synthetic construct

<400> SEQUENCE: 8
actgtgaaga tcgcttat                                                    18

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence = synthetic construct

<400> SEQUENCE: 9
gcatccttga cagccgatga ggctg                                            25
```

SIGNAL AMPLIFICATION WITH LOLLIPOP PROBES

CROSS-REFERENCE TO RELATED APPLICATIONS

This application claims benefit of U.S. Provisional Application No. 60/215,639, filed Jun. 30, 2000. Application Serial No. 60/215,639, filed Jun. 30, 2000, is hereby incorporated herein by reference.

FIELD OF THE INVENTION

The disclosed invention is generally in the field of assays for detection of nucleic acids, and specifically in the field of nucleic acid amplification.

BACKGROUND OF THE INVENTION

A number of methods have been developed which permit the implementation of extremely sensitive diagnostic assays based on nucleic acid detection. Most of these methods employ exponential amplification of targets or probes. These include the polymerase chain reaction (PCR), ligase chain reaction (LCR), self-sustained sequence replication (3SR), nucleic acid sequence based amplification (NASBA), strand displacement amplification (SDA), and amplification with Qβ replicase (Birkenmeyer and Mushahwar, *J. Virological Methods*, 35:117–126 (1991); Landegren, *Trends Genetics*, 9:199–202 (1993)).

While all of these methods offer good sensitivity, with a practical limit of detection of about 100 target molecules, all of them suffer from relatively low precision in quantitative measurements. This lack of precision manifests itself most dramatically when the diagnostic assay is implemented in multiplex format, that is, in a format designed for the simultaneous detection of several different target sequences.

Fluorescence in situ hybridization is a useful method of determining the physical position of sequences relative to each other in the genome. However, the ability to detect sequences decreases as the size of the target sequence decreases so that detection of targets that are less than 500 bases in length is very difficult or impossible.

Rolling Circle Amplification (RCA) driven by DNA polymerase can replicate circular oligonucleotide probes with either linear or geometric kinetics under isothermal conditions (Lizardi et al., *Nature Genet.* 19: 225–232 (1998); U.S. Pat. No. 5,854,033 to Lizardi; PCT Application No. WO 97/19193). If a single primer is used, RCA generates in a few minutes a linear chain of hundreds or thousands of tandemly-linked DNA copies of a target which is covalently linked to that target. Generation of a linear amplification product permits both spatial resolution and accurate quantitation of a target. DNA generated by RCA can be labeled with fluorescent oligonucleotide tags that hybridize at multiple sites in the tandem DNA sequences. RCA can be used with fluorophore combinations designed for multiparametric color coding (PCT Application No. WO 97/19193), thereby markedly increasing the number of targets that can be analyzed simultaneously. RCA technologies can be used in solution, in situ and in microarrays. In solid phase formats, detection and quantitation can be achieved at the level of single molecules (Lizardi et al., 1998).

Ligation-mediated Rolling Circle Amplification (LM-RCA) involves circularization of a probe molecule hybridized to a target sequence and subsequent rolling circle amplification of the circular probe (U.S. Pat. No. 5,854,033 to Lizardi; PCT Application No. WO 97/19193). During amplification, the probe can become separated from the target sequence as it rolls. This can diminish the quality of spatial information obtained about the target.

It is therefore an object of the present invention to provide a method and compositions for detecting nucleic acid sequences in situ with a combination of specificity and sensitivity.

It is another object of the present invention to provide a method and compositions for detecting the amount and location of nucleic acid sequences with a combination of specificity and sensitivity.

BRIEF SUMMARY OF THE INVENTION

Disclosed is a method and compositions for the sensitive detection of the amount and location of specific nucleic acid sequences. The method makes use of a branched oligomer, referred to as a lollipop oligomer, that has a tail portion, a right arm portion, and a left arm portion. These three components are joined at a common junction making a three-tailed structure. The two arms each end with sequences complementary to adjacent sequences in a target sequence. This allows the right and left arms to be ligated together when the oligomer is hybridized to the target sequence, thus topologically linking the oligomer to the target sequence. The tail portion can then be detected at the location of the target sequence. By using the tail of the oligomer to prime rolling circle replication of a DNA circle, a long tandem repeat DNA is associated with the target sequence. Rolling circle replication does not disturb association of the arms and the target sequence, thus maintaining close association of the tandem repeat DNA and the target sequence.

The topological locking of the probe to the target is important for detection systems in which the amplified product may float away from the target. This may happen if the target sequence is extremely small or if the assay is being preformed on a substrate such as a metaphase chromosomes or any array that does not trap the tandem repeat DNA. By using multiple different primer (tail) sequences and corresponding DNA circles the method can be multiplexed, with the amplification product of each different circle being separately detectable. Lollipop oligomers can be circularized by chemical or enzymatic ligation.

The disclosed method is useful for detecting any desired sequence. In particular, the disclosed method can be used to localize or amplify signal from any desired sequence. For example, the disclosed method can be used to probe transgenic cells, bacterial or yeast colonies, cellular material (for example, whole cells, DNA fibers, interphase nuclei, or metaphase chromosomes on slides, arrayed genomic DNA, RNA). The disclosed method is particularly useful for detecting sequence variants of a target sequence. For example, insertions, deletions, repeats, and single nucleotide polymorphisms (SNP), can be detected. Specificity of these detections is aided by sensitivity of ligation of the arm ends to mismatches.

The disclosed method is applicable to numerous areas including, but not limited to, disease detection, mutation detection, RNA expression profiling, gene discovery, gene mapping (molecular haplotyping), agricultural research, and virus detection. Preferred uses include SNP detection in situ in cells, on microarrays, on DNA fibers, and on genomic DNA arrays; detection of RNA in cells; RNA expression profiling; molecular haplotyping; mutation detection; abnormal RNA (for example, overexpression of an oncogene or absence of expression of a tumor suppressor gene); expression in cancer cells; detection of viral genome in cells; viral RNA expression; detection of inherited diseases such as cystic fibrosis, muscular dystrophy, diabetes, hemophilia, sickle cell anemia; assessment of predisposition for cancers such as prostate cancer, breast cancer, lung cancer, colon cancer, ovarian cancer, testicular cancer, pancreatic cancer.

DETAILED DESCRIPTION OF THE INVENTION

Figure 1:
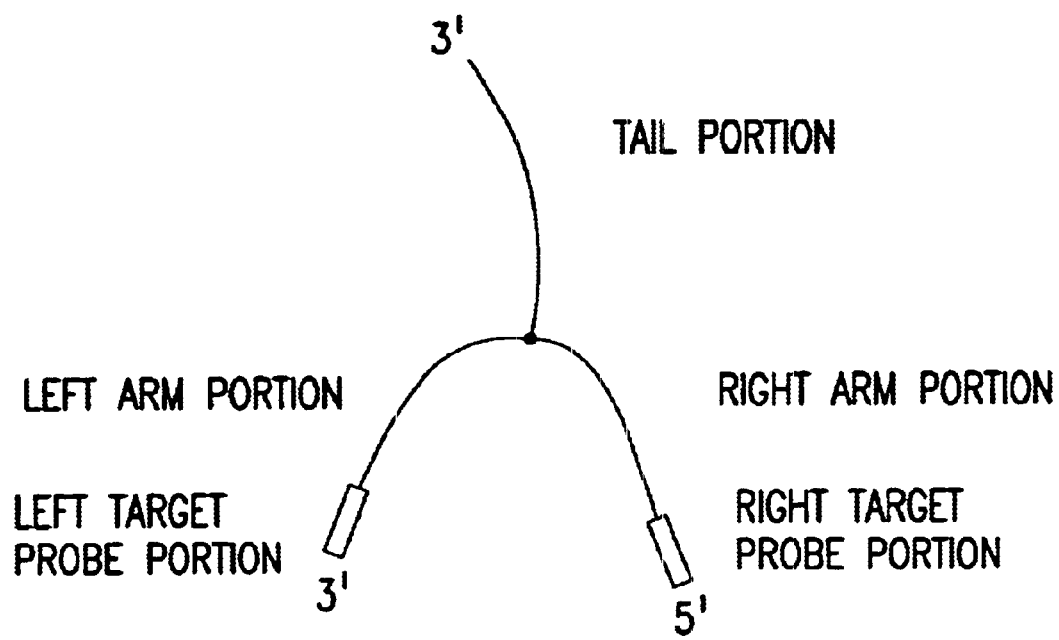
FIG. 1 is a diagram of an example of a lollipop oligomer.

The disclosed method makes use of a special branched oligomer, referred to as a lollipop oligomer, to provide sensitive and reliable detection and quantitation of target nucleic acid sequences. The disclosed method is particularly useful for detecting nucleic acid sequences where the sequences are located (that is, in situ detection). The lollipop oligomers allow isothermic signal amplification through rolling circle amplification via a tail portion of the oligomer that becomes associated or topologically linked to the target nucleic acid sequence.

The disclosed method involves mixing one or more different lollipop oligomers with one or more target samples and incubating under conditions that promote hybridization between the oligomers and target sequences in the samples. The arms of the lollipop oligomer are then ligated in a target-dependent manner. The oligomers are mixed with one or more amplification target circles and incubated under conditions that promote hybridization between the amplification target circles and the rolling circle replication primer portions of the oligomers. To amplify the signal, DNA polymerase is mixed with the oligomers and amplification target circles and incubated under conditions that promote replication of the amplification target circles. Replication of the amplification target circle results in the formation of a long DNA strand containing numerous tandem repeats of the amplification target circle sequence (the DNA is referred to as tandem sequence DNA). Unique identification of multiple nucleic acid sequences in a single assay is accomplished by associating unique tail sequences (part of the oligomer) with each the various nucleic acid sequences to be detected. Each tail sequence (acting as a rolling circle replication primer) hybridizes to, and primes replication of, a unique amplification target circle. Detection of the unique sequences of the various resulting tandem sequence DNAs (each derived from a different, nucleic acid sequence-specific amplification target circle) indicates the presence in the nucleic acid sample of the target sequence corresponding to that tandem DNA sequence. The tail sequence of lollipop oligomers can also be detected and/or amplified using other techniques.

The disclosed method is useful for detection, quantitation, and/or location of any desired nucleic acid sequences. The disclosed method can be multiplexed to detect numerous different nucleic acid sequences simultaneously or in a single assay. Thus, the disclosed method is useful for detecting, assessing, quantitating, profiling, and/or cataloging RNA expression in nucleic acid samples. The disclosed method is also particularly useful for detecting and discriminating single nucleotide differences in nucleic acid sequences. This specificity is possible due to the sensitivity of ligation of the oligomer arms to base mismatches around the ends of the arms. Thus, the disclosed method is useful for detecting, assessing, quantitating, and/or cataloging single nucleotide polymorphisms, and other sequence differences between nucleic acids, nucleic acid samples, and sources of nucleic acid samples. In particular, the ratio of different polymorphs of a nucleic acid sequence in sample can be assessed due to the ability of the disclosed method to detect single copies of target sequences.

The disclosed method is applicable to numerous areas including, but not limited to, disease detection, mutation detection, RNA expression profiling, gene discovery, gene mapping (molecular haplotyping), agricultural research, and virus detection. Preferred uses include SNP detection in situ in cells, on microarrays, on DNA fibers, and on genomic DNA arrays; detection of RNA in cells; RNA expression profiling; molecular haplotyping, mutation detection, abnormal RNA (for example, overexpression of an oncogene or absence of expression of a tumor suppressor gene), expression in cancer cells, detection of viral genome in cells, viral RNA expression; detection of inherited diseases such as cystic fibrosis, muscular dystrophy, diabetes, hemophilia, sickle cell anemia; assessment of predisposition for cancers such as prostate cancer, breast cancer, lung cancer, colon cancer, ovarian cancer, testicular cancer, pancreatic cancer.

Materials

A. Lollipop Oligomers

A lollipop oligomer is a branched oligomer including three components: a tail portion, a right arm portion and a left arm portion. In general, the tail portion, the right arm portion, and the left arm portion are coupled together, with the tail portion is coupled to the oligomer at the junction of the right arm portion and the left arm portion. However, the tail portion can be coupled to the oligomer in the right or left arm portion, but preferably not in either the right or left target probe portion. The right arm portion of an oligomer generally includes a right target probe portion and a right backbone portion. The left arm portion generally includes a left target probe portion and a left backbone portion. The right target probe portion is at the end of the right arm portion and the left target probe portion is at the end of the left arm portion. The target probe portions are complementary to a target nucleic acid sequence. The target sequence has a 5' region and a 3' region such that the left target probe portion and the right target probe portion of the oligomer are each complementary to the 3' region and the 5' region, respectively, of the target sequence. An example of a lollipop oligomer is shown in FIG. 1. Lollipop oligomers are also referred to herein as oligomer and as lollipop probes.

In general, the tail and arms of a lollipop oligomer are single-stranded oligonucleotides. The right and left arms generally contain between 25 to 500 nucleotides, preferably between about 30 to 75 nucleotides, and most preferably between about 35 to 50 nucleotides. The right arm has a 5' phosphate group and the left arm a 3' hydroxyl group. This allows the ends to be ligated using a DNA ligase, or extended in a gap-filling operation. Portions of the lollipop oligomer have specific functions making the oligomer useful for the disclosed method. In preferred embodiments, these portions are referred to as the target probe portions, the backbone portions, the tail portion, and the rolling circle replication primer portion. The target probe portions and the tail portion are required elements of a lollipop oligomer. The backbone portions and the segment of the tail portion that are not in the rolling circle replication primer portion can be arbitrarily chosen sequences or can be non-nucleotide linkers.

A particularly preferred embodiment is a lollipop oligomer with right and left arms of 35 to 50 nucleotides each, including a left target probe of 20 nucleotides and a right target probe of 20 nucleotides. The left target probe and right target probe hybridize to a target sequence leaving a gap of five nucleotides, which is filled by a single pentanucleotide gap oligonucleotide. Another preferred embodiment is a lollipop oligomer with right and left arms of 35 to 50 nucleotides each, including a right target probe with a fixed length (preferably 20 nucleotides) and left target probe with a variable length (preferably 10 to 20 nucleotides) for maximal discrimination of single nucleotide polymorphisms. Lollipop oligomers hybridized to a target sequence and having ligated ends are referred to as locked lollipop oligomers.

1. Tail Portion

The tail portion of a lollipop oligomer is used as a signal, or to generate a signal, when the oligomer is associated with a target sequence. The tail portion can have any structure or composition that achieves this signaling purpose. It is preferred that the tail portion include a rolling circle replication primer portion or an address tag portion.

Rolling Circle Replication Primer Portions

A rolling circle replication primer (RCRP) portion is a portion of a tail portion having sequence complementary to the primer complement portion of an amplification target circle. This sequence is referred to as the complementary portion of the RCRP portion. The complementary portion of a RCRP portion and the cognate primer complement portion can have any desired sequence so long as they are complementary to each other. In general, the sequence of the RCRP portion can be chosen such that it is not significantly complementary to any other portion of the amplification target circle. The complementary portion of a rolling circle replication primer portion can be any length that supports specific and stable hybridization between the primer and the primer complement portion. Generally this is 10 to 35 nucleotides long, but is preferably 16 to 20 nucleotides long.

Address Tag Portions

An address tag portion is part of the tail portion that has a sequence matching the sequence of the complementary portion of an address probe. This address tag portion allows detection of the lollipop oligomer through hybridization of amplification mediated by the address tag portion. If present, there may be one, or more than one, address tag portion on a lollipop oligomer. It is preferred that a lollipop oligomer have one or two address tag portions. Most preferably, an oligomer will have one address tag portion. Generally, it is preferred that an oligomer have 50 address tag portions or less. There is no fundamental limit to the number of address tag portions that can be present on an oligomer except the size of the tail portion of the oligomer. When there are multiple address tag portions, they may have the same sequence or they may have different sequences, with each different sequence complementary to a different address probe. It is preferred that a lollipop oligomer contain address tag portions that have the same sequence such that they are all complementary to a single address probe. The address tag portion can be any length that supports specific and stable hybridization between the address tag and the address probe. For this purpose, a length between 10 and 35 nucleotides long is preferred, with an address tag portion 15 to 20 nucleotides long being most preferred.

2. Arm Portions

The left and right arm portions carry the target probe portions that allow sequence-specific association of the lollipop oligomer with a target sequence. Left and right backbone portions provide flexibility and connect the target probe portions to each other and to the tail portion. The backbone portions can have any arbitrary sequence and, in fact, need not contain nucleotides or base moieties at all. However, it is preferred that one or both of the backbone portions be designed to form intramolecular associations with the tail portions. Such associations are designed to keep the tail portion (or at least the rolling circle replication portion) inaccessible to an amplification target circle unless the oligomer is hybridized to a target sequence. This can be accomplished, for example, by having one or both of the arm portions associate with the tail portion. For example, the tail portion can be designed to be complementary to all or a portion of the right backbone portion, all or a portion of the left backbone portion, or a portion of the right backbone portion and a portion of the left backbone portion. Hybridization of the tail portion to either or both of the backbone portions will make the tail portion inaccessible to the amplification target circle. The backbone portions and the tail portion can also be designed to form a triple helix, which also makes the tail portion inaccessible to the amplification target circle.

Target Probe Portions

There are two target probe portions on each lollipop oligomer, one at each end of the oligomer arms. The target probe portions can each be any length that supports specific and stable hybridization between the target probes and the target sequence. For this purpose, a length of 10 to 35 nucleotides for each target probe portion is preferred, with target probe portions 15 to 20 nucleotides long being most preferred. The target probe portion at the 3' end of the lollipop oligomer is referred to as the left target probe, and the target probe portion at the 5' end of the oligomer is referred to as the right target probe. These target probe portions are also referred to herein as left and right target probes or left and right probes. The target probe portions are complementary to a target nucleic acid sequence.

Figure 2A:
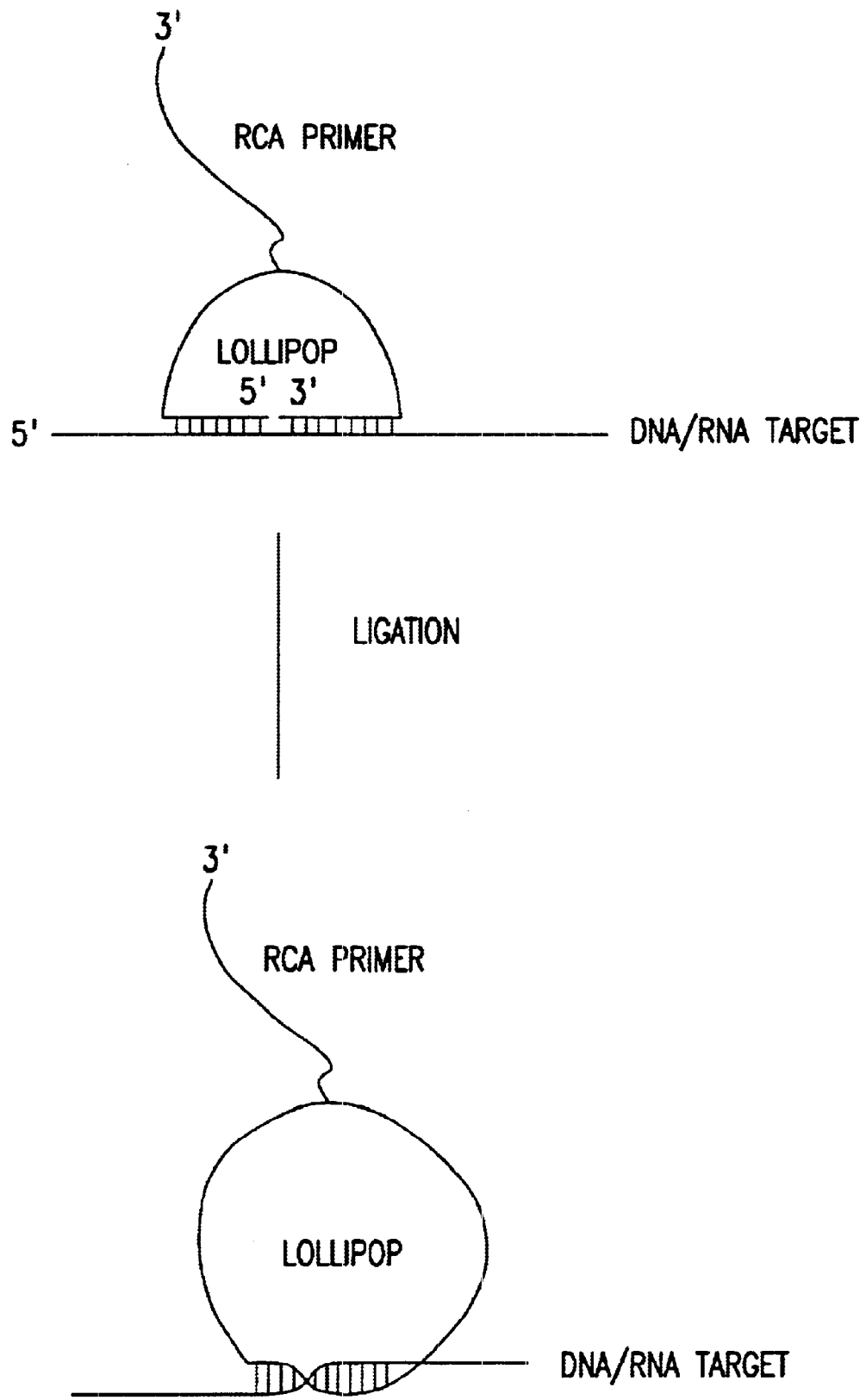
FIGS. 2A and 2B are diagrams of an example of detection of a DNA or RNA target sequence using a lollipop oligomer and rolling circle amplification.
Figure 2B:
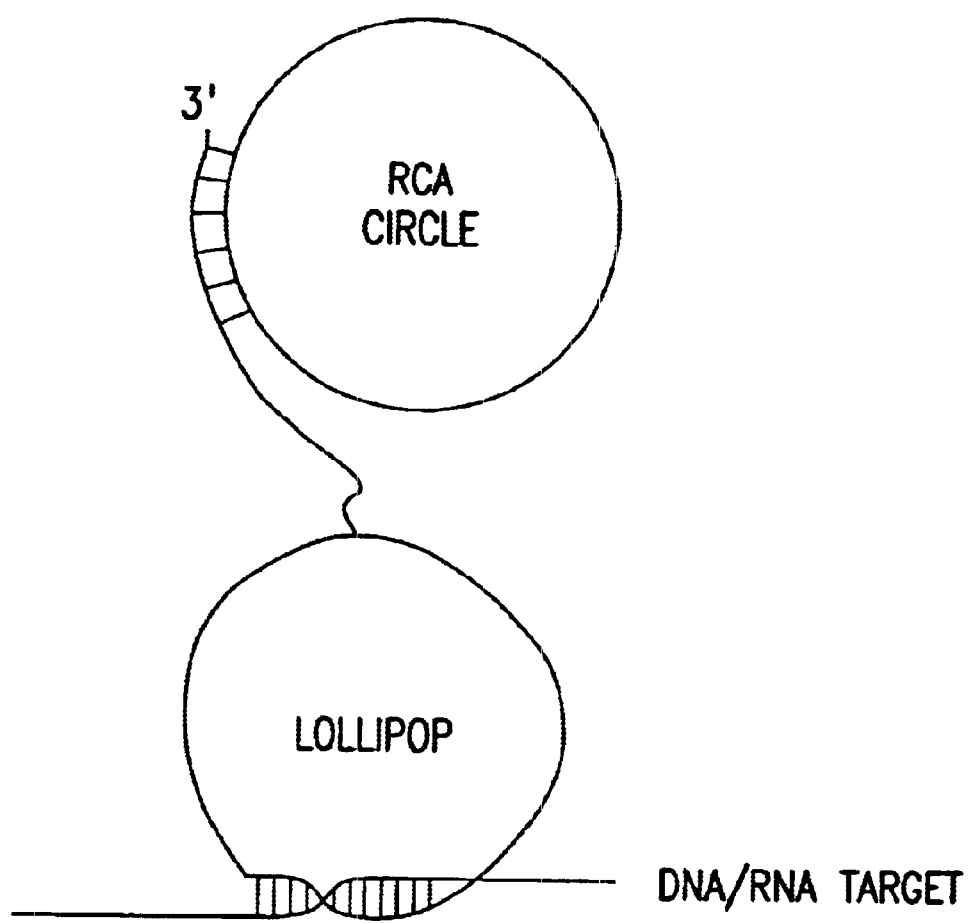

The target probe portions are complementary to the target sequence, such that upon hybridization the 5' end of the right target probe portion and the 3' end of the left target probe portion are base-paired to adjacent nucleotides in the target sequence, with the objective that they serve as a substrate for ligation or covalent coupling (FIG. 2A). Optionally, the 5' end and the 3' end of the target probe portions may hybridize in such a way that they are separated by a gap space. In this case the 5' end and the 3' end of the oligomer may only be ligated if one or more additional oligonucleotides, referred to as gap oligonucleotides, are used, or if the gap space is filled during the ligation operation. The gap oligonucleotides hybridize to the target sequence in the gap space to a form continuous probe/target hybrid. The gap space may be any length desired but is generally ten nucleotides or less. It is preferred that the gap space is between about three to ten nucleotides in length, with a gap space of four to eight nucleotides in length being most preferred. Alternatively, a gap space could be filled using a DNA polymerase before or during the ligation operation. When using such a gap-filling operation, a gap space of three to five nucleotides in length is most preferred. As another alternative, the gap space can be partially bridged by one or more gap oligonucleotides, with the remainder of the gap filled using DNA polymerase.

The target probe portions are preferably designed to be complementary to a polymorphic or variable nucleotide position at the end of the right target probe portion, the left target probe portion, or both. The oligomer ends will be effectively ligated only in the presence of the corresponding form of the target sequence (not a form of the target sequence having a different nucleotide at that position) since effective ligation of the ends requires that the terminal nucleotides be base paired to complementary nucleotides. Similar effects can be achieved with the use of gap oligonucleotides. In this case, the gap oligonucleotide is designed to be complementary to the polymorphic or variable nucleotide(s) in the target sequence. If the gap oligonucleotide is short, even a single internal base mismatch can prevent effective ligation by destabilizing hybridization of the gap oligonucleotide.

3. Composition

Lollipop oligomers can have any composition that allows the target probe portions to hybridize to the corresponding target sequence and the tail portion to mediate detection and/or signal amplification. Preferably, the tail portion, right arm portion, and left arm portion are oligonucleotides. The right target probe portion and the left target probe portion can also be, or include regions of, peptide nucleic acids and other oligonucleotide analogues. The oligomers can also include nucleoside and nucleotide analogues. In particular, the arms and tail can also be chimeric; containing any combination of standard nucleotides, nucleotide analogues, nucleoside analogues, and oligonucleotide analogues.

The tail portion and arm portions of oligomers can be joined in any manner that allows the oligomer to function as described herein. In one form, the left and right arm portions together can be a single oligonucleotide or oligomer strand with the tail portion cross linked to one of the nucleotides in the arm oligonucleotide (thus defining the two arm portions). Alternatively, the tail portion and one of the arm portions together can be a single oligonucleotide with the other arm portion cross linked to it. Lollipop oligomers can also include linkers. In the context of a lollipop oligomer, a linker is any non-nucleotide chain, structure, or region that links two or more of the components of the lollipop oligomer together. For example, in one form, at least a portion of the tail portion, right arm portion, or left arm portion of the oligomer is a linker. In particular, the junction between the tail and arms can be a branched linker structure. Any core or branched structure can form the junction of the tail and arm portions of the oligomer. All that is required is that the arms and the tail can be linked or coupled to the junction structure. Many coupling chemistries are known and can be adapted for use in linking components of lollipop oligomers.

As used herein, oligomer refers to oligomeric molecules composed of subunits where the subunits can be of the same class (such as nucleotides) or a mixture of classes (such as nucleotides and ethylene glycol). It is preferred that the disclosed lollipop oligomers be oligomeric sequences, non-nucleotide linkers, or a combination of oligomeric sequences and non-nucleotide linkers. It is more preferred that the disclosed lollipop oligomers be oligomeric sequences. Oligomeric sequences are oligomeric molecules where each of the subunits includes a nucleobase (that is, the base portion of a nucleotide or nucleotide analogue) which can interact with other oligomeric sequences in a base-specific manner. The hybridization of nucleic acid strands is a preferred example of such base-specific interactions. Oligomeric sequences preferably are comprised of nucleotides, nucleotide analogues, or both, or are oligonucleotide analogues. The use of the term lollipop "oligomer" is not intended to limit the disclosed lollipop structures to oligomer subunits as defined above. For example, the disclosed lollipop oligomers can include a non-oligomeric junction structure.

Non-nucleotide linkers can be any molecule, which is not an oligomeric sequence, that can be covalently coupled to an oligomeric sequence. Preferred non-nucleotide linkers are oligomeric molecules formed of non-nucleotide subunits. Examples of such non-nucleotide linkers are described by Letsinger and Wu, (*J. Am. Chem. Soc.* 117:7323–7328 (1995)), Benseler et al., (*J. Am. Chem. Soc.* 115:8483–8484 (1993)) and Fu et al., (*J. Am. Chem. Soc.* 116:4591–4598 (1994)). Preferred non-nucleotide linkers, or subunits for non-nucleotide linkers, include substituted or unsubstituted $C_1$–$C_{18}$ straight chain or branched alkyl, substituted or unsubstituted $C_2$–$C_{18}$ straight chain or branched alkenyl, substituted or unsubstituted $C_2$–$C_{18}$ straight chain or branched alkynyl, substituted or unsubstituted $C_1$–$C_{18}$ straight chain or branched alkoxy, substituted or unsubstituted $C_2$–$C_{18}$ straight chain or branched alkenyloxy, and substituted or unsubstituted $C_2$–$C_{18}$ straight chain or branched alkynyloxy. The substituents for these preferred non-nucleotide linkers (or subunits) can be halogen, cyano, amino, carboxy, ester, ether, carboxamide, hydroxy, or mercapto.

As used herein, nucleoside refers to adenosine, guanosine, cytidine, uridine, 2'-deoxyadenosine, 2'-deoxyguanosine, 2'-deoxycytidine, or thymidine. A nucleoside analogue is a chemically modified form of nucleoside containing a chemical modification at any position on the base or sugar portion of the nucleoside. As used herein, nucleotide refers to a phosphate derivative of nucleosides as described above, and a nucleotide analogue is a phosphate derivative of nucleoside analogues as described above. The subunits of oligonucleotide analogues, such as peptide nucleic acids, are also considered to be nucleotide analogues.

As used herein, oligonucleotide analogues are polymers of nucleic acid-like material with nucleic acid-like properties (such as sequence dependent hybridization) that contain, at one or more positions, a modification away from a standard RNA or DNA nucleotide. A preferred example of an oligonucleotide analogue is peptide nucleic acid. The internucleosidic linkage between two nucleosides can be achieved by phosphodiester bonds or by modified phospho bonds such as by phosphorothioate groups or other bonds such as, for example, those described in U.S. Pat. No. 5,334,711.

B. Target Sequences

As used herein, a target sequence is a nucleic acid sequence to which the disclosed target probe portions (and gap oligonucleotides) are associated. Any nucleic acid molecule can include a target sequence for use in the disclosed method. Preferred target sequences are in naturally occurring DNA molecules and RNA molecules such as mRNA, viral RNA, and ribosomal RNA.

The target samples containing target sequences can come from any source. For example, target sequences can be obtained from mRNA samples, nucleic acid libraries, cells, cultures, tissues, bodily fluids, urine, serum, biopsy samples, and environmental samples. Numerous other sources of nucleic acids are known or can be developed and any can be used with the disclosed method. Any nucleic acid sample can be used as a target sample in the disclosed method. Examples of suitable target samples include mRNA samples, nucleic acid libraries, whole cell samples, environmental samples, culture samples, tissue samples, bodily fluids, urine samples, serum samples, and biopsy samples. Numerous other sources of target samples are known or can be developed and any can be used with the disclosed method.

A target sample is any solution or composition containing or potentially containing a target sequence. A target sample can take any form. A preferred form of target sample is a solid state target.

C. Amplification Target Circles

An amplification target circle (ATC) is a circular single-stranded DNA molecule, generally containing between 40 to 1000 nucleotides, preferably between about 50 to 150 nucleotides, and most preferably between about 50 to 100 nucleotides. Portions of ATCs have specific functions making the ATC useful for rolling circle amplification (RCA). These portions are referred to as the primer complement portion, the detection tag portions, the secondary target sequence portions, the address tag portions, and the promoter portion. The primer complement portion is a required element of an amplification target circle. Detection tag portions, secondary target sequence portions, address tag portions, and promoter portions are optional. Generally, an amplification target circle is a single-stranded, circular DNA molecule comprising a primer complement portion. Those segments of the ATC that do not correspond to a specific portion of the ATC can be arbitrarily chosen sequences. It is preferred that ATCs do not have any sequences that are self-complementary. It is considered that this condition is met if there are no complementary regions greater than six nucleotides long without a mismatch or gap. It is also preferred that ATCs containing a promoter portion do not have any sequences that resemble a transcription terminator, such as a run of eight or more thymidine nucleotides.

An amplification target circle, when replicated, gives rise to a long DNA molecule containing multiple repeats of sequences complementary to the amplification target circle. This long DNA molecule is referred to herein as tandem sequences DNA (TS-DNA). TS-DNA contains sequences complementary to the primer complement portion and, if present on the amplification target circle, the detection tag portions, the secondary target sequence portions, the address tag portions, and the promoter portion. These sequences in the TS-DNA are referred to as primer sequences (which match the sequence of the rolling circle replication primer), spacer sequences (complementary to the spacer region), detection tags, secondary target sequences, address tags, and promoter sequences. Amplification target circles are useful as tags for specific binding molecules.

D. Tandem Sequence DNA

An amplification target circle, when replicated, gives rise to a long DNA molecule containing multiple repeats of sequences complementary to the circular vector. This long DNA molecule is referred to herein as tandem sequences DNA (TS-DNA). TS-DNA contains sequences complementary to the inserted nucleic acid molecule and the primer complement portion. If the tandem sequence DNA is itself replicated by strand displacement amplification, the resulting long DNA molecules containing multiple repeats of sequences matching the circular vector are referred to as secondary tandem sequence DNA. If the secondary tandem sequence DNA is in turn replicated by strand displacement amplification, the resulting long DNA molecules containing multiple repeats of sequences complementary to the circular vector are referred to as tertiary tandem sequence DNA.

E. Solid State Targets

The target sample and target sequences can be coupled to a substrate. Doing so is useful for a variety of purposes including immobilization of the reaction or reaction products, allowing easy washing of reagents and reactions during an assay, aiding identification or detection of ligated probes, and making it easier to assay multiple samples simultaneously. In particular, immobilization of target sequences allows the location of the target sequences in a sample or array to be determined. For example, a cell or chromosome spread can be probed in the disclosed method to determine the presence and location of specific target sequences within a cell, genome, or chromosome.

Solid-state substrates to which target samples can be attached can include any solid material to which nucleic acids can be attached, adhered, or coupled, either directly or indirectly. This includes materials such as acrylamide, cellulose, nitrocellulose, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, fibers, woven fibers, optical fibers, shaped polymers, particles and microparticles. Preferred forms for solid-state substrates are flat surfaces, especially those used for cell and chromosome spreads.

Methods for immobilization of nucleic acids to solid-state substrates are well established. In general, target samples can be immobilized on a substrate as part of a nucleic acid sample or other sample containing target sequences. Target sequences can be coupled to substrates using established coupling methods. For example, suitable attachment methods are described by Pease et al., *Proc. Natl. Acad. Sci. USA* 91(11):5022–5026 (1994), Guo et al., *Nucleic Acids Res.* 22:5456–5465 (1994), and Khrapko et al., *Mol Biol (Mosk) (USSR)* 25:718–730 (1991). A method for immobilization of 3'-amine oligonucleotides on casein-coated slides is described by Stimpson et al., *Proc. Natl. Acad. Sci. USA* 92:6379–6383 (1995).

Methods for producing arrays of nucleic acids on solid-state substrates are also known. Examples of such techniques are described in U.S. Pat. No. 5,871,928 to Fodor et al., U.S. Pat. No. 5,54,413, U.S. Pat. No. 5,429,807, and U.S. Pat. No. 5,599,695 to Pease et al. Microarrays of RNA targets can be fabricated, for example, using the method described by Schena et al., *Science* 270:487–470 (1995).

Although preferred, it is not required that a given array of target samples or sequences be a single unit or structure. The set of probes may be distributed over any number of solid supports. For example, at one extreme, each target sequence or each target sample may be immobilized in or on a separate surface, reaction tube, container, fiber, or bead.

A variety of cell and nucleic acid sample preparation techniques are known and can be used to prepare samples for use in the disclosed method. For example, metaphase chromosomes and interphase nuclei can be prepared as described by Cremer et al., *Hum Genet* 80(3):235–46 (1988), and Haaf and Ward, *Hum Mol Genet* 3(4): 629–33 (1994), genomic DNA fibers can be prepared as described by Yunis et al., *Chromosoma* 67(4):293–307 (1978), and Parra and Windle, *Nature Genet.* 5:17–21 (1993), and Halo preparations can be prepared as described by Vogelstein et al., *Cell* 22(1 Pt 1):79–85 (1980), and Wiegant et al., *Hum Mol Genet.* 1(8):587–91 (1992).

F. Gap Oligonucleotides

Figure 3:
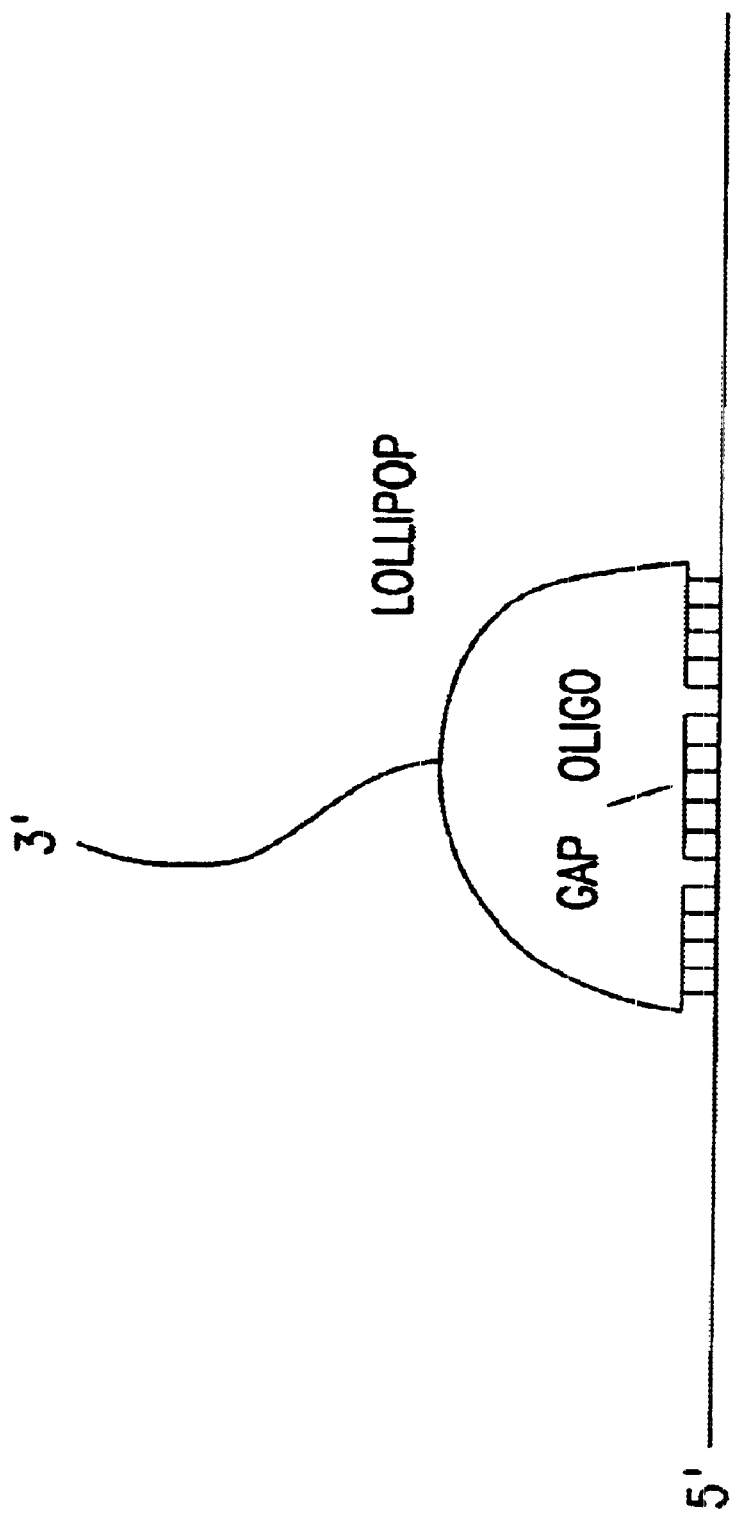
FIG. 3 is a diagram of a lollipop oligomer and a gap oligonucleotide hybridized to a target sequence. The oligomer leaves a gap space when hybridized to the target sequence and the gap oligonucleotide hybridizes to the target sequence in the gap space.

Gap oligonucleotides are oligonucleotides that are complementary to all or a part of that portion of a target sequence which covers a gap space between the ends of a hybridized lollipop oligomer. An example of a gap oligonucleotide and its relationship to a target sequence and open circle probe is shown in FIG. 3. Gap oligonucleotides have a phosphate group at their 5' ends and a hydroxyl group at their 3' ends. This facilitates ligation of gap oligonucleotides to open circle probes, or to other gap oligonucleotides. The gap space between the ends of a hybridized lollipop oligomer can be filled with a single gap oligonucleotide, or it can be filled with multiple gap oligonucleotides. For example, two three nucleotide gap oligonucleotides can be used to fill a six nucleotide gap space, or a three nucleotide gap oligonucleotide and a four nucleotide gap oligonucleotide can be used to fill a seven nucleotide gap space. Gap oligonucleotides are particularly useful for distinguishing between closely related target sequences. For example, multiple gap oligonucleotides can be used to amplify different allelic or other variants of a target sequence. By placing the region of the target sequence in which the variation occurs in the gap space formed by a lollipop oligomer, a single lollipop oligomer can be used to amplify each of the individual variants by using an appropriate set of gap oligonucleotides.

G. Strand Displacement Primers

Primers used for strand displacement replication are referred to herein as strand displacement primers. One form of strand displacement primer, referred to herein as a secondary strand displacement primer, is an oligonucleotide having sequence matching part of the sequence of an amplification target circle. This sequence is referred to as the matching portion of the strand displacement primer. This matching portion of a secondary strand displacement primer is complementary to sequences in tandem sequence DNA (TS-DNA). The matching portion of a secondary strand displacement primer may be complementary to any sequence in TS-DNA. However, it is preferred that it not be complementary TS-DNA sequence matching either the rolling circle replication primer portion of a lollipop oligomer or a tertiary strand displacement primer, if one is being used. This prevents hybridization of the primers to each other. The matching portion of a strand displacement primer can be any length that supports specific and stable hybridization between the primer and its complement. Generally this is 12 to 35 nucleotides long, but is preferably 18 to 25 nucleotides long. It is preferred that the matching portion of the circular vector is near the 3' end of the first strand of the circular vector.

It is preferred that secondary strand displacement primers also contain additional sequence at their 5' end that does not match any part of the first strand of the circular vector. This sequence is referred to as the non-matching portion of the strand displacement primer. The non-matching portion of the strand displacement primer, if present, serves to facilitate strand displacement during DNA replication. The non-matching portion of a strand displacement primer may be any length, but is generally 1 to 100 nucleotides long, and preferably 4 to 8 nucleotides long.

Another form of strand displacement primer, referred to herein as a tertiary strand displacement primer, is an oligonucleotide having sequence complementary to part of the sequence of an amplification target circle. This sequence is referred to as the complementary portion of the tertiary strand displacement primer. This complementary portion of the tertiary strand displacement primer matches sequences in TS-DNA. The complementary portion of a tertiary strand displacement primer may be complementary to any sequence in the first strand of the circular vector. However, it is preferred that it not be complementary to a sequence matching the strand displacement primer. This prevents hybridization of the primers to each other. The complementary portion of a tertiary strand displacement primer can be any length that supports specific and stable hybridization between the primer and its complement. Generally this is 12 to 35 nucleotides long, but is preferably 18 to 25 nucleotides long. It is preferred that tertiary strand displacement primers also contain additional sequence at their 5' end that is not complementary to any part of the first strand of the circular vector. This sequence is referred to as the non-complementary portion of the tertiary strand displacement primer. The non-complementary portion of the tertiary strand displacement primer, if present, serves to facilitate strand displacement during DNA replication. The non-complementary portion of a tertiary strand displacement primer may be any length, but is generally 1 to 100 nucleotides long, and preferably 4 to 8 nucleotides long.

Strand displacement primers may also include modified nucleotides to make them resistant to exonuclease digestion. For example, the primer can have three or four phosphorothioate linkages between nucleotides at the 5' end of the primer. Such nuclease resistant primers allow selective degradation of excess unligated lollipop oligomers that might otherwise interfere with hybridization of probes and primers to the amplified nucleic acid. Strand displacement primers can be used for strand displacement replication and strand displacement cascade amplification, both described in U.S. Pat. No. 5,854,033 and PCT Application No. WO 97/19193.

H. Address Probes

An address probe is an oligonucleotide or polynucleotide having a sequence complementary to address tags on the tail portion of a lollipop oligomer, TS-DNA, or transcripts of TS-DNA. The complementary portion of an address probe can be any length that supports specific and stable hybridization between the address probe and the address tag. For this purpose, a length of 10 to 35 nucleotides is preferred, with a complementary portion of an address probe 12 to 18 nucleotides long being most preferred. Address probes can contain a single complementary portion or multiple complementary portions.

Address probes can also numerous labels or detection tag sequences to increase the signal from any target sequence with which the address probe becomes associated (via a lollipop oligomer). For example, an address probe can be branched to increase the density of labels or tag sequences. Address probe can also contain sequences that can be amplified using a nucleic acid amplification technique, including PCR and RCA.

I. Synthesis of Oligonucleotides

Lollipop oligomers, components of lollipop oligomers, strand displacement primers, and any other oligonucleotides can be synthesized using established oligonucleotide synthesis methods. Methods to produce or synthesize oligonucleotides are well known in the art. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323–356 (1984), (phosphotriester and phosphite-triester methods), and Narang et al., *Methods Enzymol.* 65:610–620 (1980), (phosphotriester method). Protein nucleic acid molecules can be made using known methods such as those described by Nielsen et al., *Bioconjug. Chem.* 5:3–7 (1994).

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, *Biochemistry* 34:10807–10815 (1995), McGraw et al., *Biotechniques* 8:674–678 (1990), and Rychlik et al., *Nucleic Acids Res.* 18:6409–6412 (1990).

J. Detection Probes

Detection probes are labeled oligonucleotides having sequence complementary to detection tags on TS-DNA, transcripts of TS-DNA, or address probes. The complementary portion of a detection probe can be any length that supports specific and stable hybridization between the detection probe and the detection tag. For this purpose, a length of 10 to 35 nucleotides is preferred, with a complementary portion of a detection probe 16 to 20 nucleotides long being most preferred. Detection probes can contain any of the detection labels described below. Preferred labels are biotin and fluorescent molecules. A particularly preferred detection probe is a molecular beacon. Molecular beacons are detection probes labeled with fluorescent moieties where the fluorescent moieties fluoresce only when the detection probe is hybridized (Tyagi and Kramer, *Nature Biotechnology* 14:303–308 (1996)). The use of such probes eliminates the need for removal of unhybridized probes prior to label detection because the unhybridized detection probes will not produce a signal. This is especially useful in multiplex assays.

A preferred form of detection probe, referred to herein as a collapsing detection probe, contains two separate complementary portions. This allows each detection probe to hybridize to two detection tags in TS-DNA. In this way, the detection probe forms a bridge between different parts of the TS-DNA. The combined action of numerous collapsing detection probes hybridizing to TS-DNA will be to form a collapsed network of cross-linked TS-DNA. Collapsed TS-DNA occupies a much smaller volume than free, extended TS-DNA, and includes whatever detection label present on the detection probe. This result is a compact and discrete detectable signal for each TS-DNA. Collapsing TS-DNA is useful both for in situ hybridization applications and for multiplex detection because it allows detectable signals to be spatially separate even when closely packed. Collapsing TS-DNA is especially preferred for use with combinatorial multicolor coding.

TS-DNA collapse can also be accomplished through the use of ligand/ligand binding pairs (such as biotin and avidin) or hapten/antibody pairs. A nucleotide analog, BUDR, can be incorporated into TS-DNA during rolling circle replication. When biotinylated antibodies specific for BUDR and avidin are added, a cross-linked network of TS-DNA forms, bridged by avidin-biotin-antibody conjugates, and the TS-DNA collapses into a compact structure. Collapsing detection probes and biotin-mediated collapse can also be used together to collapse TS-DNA.

K. Detection Labels

To aid in detection and quantitation of ligated DNA probes, labels can be incorporated into, or coupled to, DNA probes. A label is any molecule that can be associated with DNA probes, directly or indirectly, and which results in a measurable, detectable signal, either directly or indirectly. Many such labels for incorporation into nucleic acids or coupling to nucleic acids are known. Examples of labels suitable for use in the disclosed method are radioactive isotopes, fluorescent molecules, phosphorescent molecules, enzymes, antibodies, and ligands.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester) and rhodamine (5,6-tetramethyl rhodamine). Preferred fluorescent labels for simultaneous detection are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, Oreg. and Research Organics, Cleveland, Ohio.

Labeled nucleotides are a preferred form of label since they can be directly incorporated into DNA probes during synthesis. Examples of labels that can be incorporated into DNA or RNA include nucleotide analogs such as BrdUrd (Hoy and Schimke, *Mutation Research* 290:217–230 (1993)), BrUTP (Wansick et al., *J. Cell Biology* 122:283–293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359–364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226–3232 (1994)). A preferred nucleotide analog detection label for DNA is BrdUrd (BUDR triphosphate, Sigma), and a preferred nucleotide analog detection label for RNA is Biotin-16-uridine-5'-triphosphate (Biotin-16-dUTP, Boehringher Mannheim). Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Labels that are incorporated into nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [3.3.1.1$^{3,7}$]decane]-4-yl) phenyl phosphate; Tropix, Inc.).

Methods for detecting and measuring signals generated by labels are known. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. Such methods can be used directly in the disclosed method of amplification and detection. As used herein, detection molecules are molecules which interact with amplified nucleic acid and to which one or more detection labels are coupled.

L. DNA Polymerases

DNA polymerases useful in rolling circle replication must perform rolling circle replication of primed single-stranded circles. Such polymerases are referred to herein as rolling circle DNA polymerases. For rolling circle replication, it is preferred that a DNA polymerase be capable of displacing the strand complementary to the template strand, termed strand displacement, and lack a 5' to 3' exonuclease activity. Strand displacement is necessary to result in synthesis of multiple tandem copies of the circular vector. A 5' to 3' exonuclease activity, if present, might result in the destruction of the synthesized strand. The suitability of a DNA polymerase for use in the disclosed method can be readily determined by assessing its ability to carry out rolling circle replication. Preferred rolling circle DNA polymerases are bacteriophage φ29 DNA polymerase (U.S. Pat. Nos. 5,198, 543 and 5,001,050 to Blanco et al.), phage M2 DNA polymerase (Matsumoto et al., *Gene* 84:247 (1989)), phage φPRD1 DNA polymerase (Jung et al., *Proc. Natl. Acad. Sci. USA* 84:8287 (1987)), VENT® DNA polymerase (Kong et al., *J. Biol. Chem.* 268:1965–1975 (1993)), Klenow fragment of *E. coli* DNA polymerase I (Jacobsen et al., *Eur. J. Biochem.* 45:623–627 (1974)), T5 DNA polymerase (Chatterjee et al., *Gene* 97:13–19 (1991)), PRD1 DNA polymerase (Zhu and Ito, *Biochim. Biophys. Acta.* 1219:267–276 (1994)), T7 DNA polymerase (Tabor and Richardson, *J. Biol. Chem.* 262:15330–15333 (1987); Tabor and Richardson, *J. Biol. Chem.* 264:6447–6458 (1989); T7 Sequenasem™ (U.S. Biochemicals)), ΔTts Polymerase (Amersham Pharmacia Biotech), and T4 DNA polymerase holoenzyme (Kaboord and Benkovic, *Curr. Biol.* 5:149–157 (1995)). φ29 DNA polymerase is most preferred. Rolling circle DNA polymerases are also generally useful for strand displacement replication.

Strand displacement can be facilitated through the use of a strand displacement factor, such as helicase. It is considered that any DNA polymerase that can perform rolling circle replication in the presence of a strand displacement factor is suitable for use in the disclosed method, even if the DNA polymerase does not perform rolling circle replication in the absence of such a factor. Strand displacement factors useful in RCA include, but are not limited to, BMRF1 polymerase accessory subunit (Tsurumi et al., *J. Virology* 67(12):7648–7653 (1993)), adenovirus DNA-binding protein (Zijderveld and van der Vliet, *J. Virology* 68(2): 1158–1164 (1994)), herpes simplex viral protein ICP8 (Boehmer and Lehman, *J. Virology* 67(2):711–715 (1993); Skaliter and Lehman, *Proc. Natl. Acad. Sci. USA* 91(22): 10665–10669 (1994)), single-stranded DNA binding proteins (SSB; Rigler and Romano, *J. Biol. Chem.* 270:8910–8919 (1995)), and calf thymus helicase (Siegel et al., *J. Biol. Chem.* 267:13629–13635 (1992)).

The ability of a polymerase to carry out rolling circle replication can be determined by using the polymerase in a rolling circle replication assay such as those described in Fire and Xu, *Proc. Natl. Acad. Sci. USA* 92:4641–4645 (1995).

It is possible to enhance the specificity of the DNA amplification reactions used in the disclosed method by using a DNA polymerase that is inactive at low temperature, and active only at high temperature. An example of such an enzyme, AmpliTaq Gold, has been described by Moretti et al., *Biotechniques* 25:716–722 (1998). AmpliTaq Gold is inactive until heated during the PCR before thermal cycling. A similar enzyme could be used in the disclosed method. Temperature activation of DNA polymerase can also be achieved using antibodies specific for the polymerase. For example, antibodies specific for Bst large fragment DNA polymerase could be obtained by immunization of mice. Among such antibodies, one could be chosen on the basis of its ability to bind to and inhibit the enzyme at room temperature. The antibody could also be chosen, using known screening procedures, such that upon heating, the inhibition of the DNA polymerase would cease. Combining the antibody with Bst large fragment DNA polymerase would generate an enzyme mixture that is activated upon heating.

Another type of DNA polymerase can be used if a gap-filling synthesis step is used. When using a DNA polymerase to fill gaps, strand displacement by the DNA polymerase is undesirable. Such DNA polymerases are referred to herein as gap-filling DNA polymerases. Unless otherwise indicated, a DNA polymerase referred to herein without specifying it as a rolling circle DNA polymerase or a gap-filling DNA polymerase, is understood to be a rolling circle DNA polymerase and not a gap-filling DNA polymerase. Preferred gap-filling DNA polymerases are T7 DNA polymerase (Studier et al., *Methods Enzymol.* 185:60–89 (1990)), DEEP VENT® DNA polymerase (New England Biolabs, Beverly, Mass.), modified T7 DNA polymerase (Tabor and Richardson, *J. Biol. Chem.* 262:15330–15333 (1987); Tabor and Richardson, *J. Biol. Chem.* 264:6447–6458 (1989); Sequenase™ (U.S. Biochemicals)), and T4 DNA polymerase (Kunkel et al., *Methods Enzymol.* 154:367–382 (1987)). An especially preferred type of gap-filling DNA polymerase is the *Thermusflavus* DNA polymerase (MBR, Milwaukee, Wis.). The most preferred gap-filling DNA polymerase is the Stoffel fragment of Taq DNA polymerase (Lawyer et al., *PCR Methods Appl.* 2(4): 275–287 (1993), King et al., *J. Biol. Chem.* 269(18): 13061–13064 (1994)).

M. Ligases

Any ligase is suitable for use in the disclosed method. Preferred ligases are those that preferentially form phosphodiester bonds at nicks in double-stranded DNA. That is, ligases that fail to ligate the free ends of single-stranded DNA at a significant rate are preferred. Thermostable ligases are especially preferred. Many suitable ligases are known, such as T4 DNA ligase (Davis et al., *Advanced Bacterial Genetics—A Manual for Genetic Engineering* (Cold Spring Harbor Laboratory, Cold Spring Harbor, N.Y., 1980)), *E. coli* DNA ligase (Panasnko et al., *J. Biol. Chem.* 253:4590–4592 (1978)), AMPLIGASE® (Kalin et al., *Mutat. Res.*, 283(2):119–123 (1992); Winn-Deen et al., *Mol*

*Cell Probes* (England) 7(3):179–186 (1993)), Taq DNA ligase (Barany, *Proc. Natl. Acad. Sci. USA* 88:189–193 (1991), *Thermus thermophilus* DNA ligase (Abbott Laboratories), *Thermus scotoductus* DNA ligase and *Rhodothermus marinus* DNA ligase (Thorbjarnardottir et al., *Gene* 151:177–180 (1995)). T4 DNA ligase is preferred for ligations involving RNA target sequences due to its ability to ligate DNA ends involved in DNA:RNA hybrids (Hsuih et al., *Quantitative detection of HCV RNA using novel ligation-dependent polymerase chain reaction*, American Association for the Study of Liver Diseases (Chicago, Ill., Nov. 3–7, 1995)). T4 RNA ligase can also be used to ligate DNA ends of nucleic acid strands hybridized to an RNA strand.

N. Kits

Any combination of the materials useful in the disclosed method can be packaged together as a kit for performing the disclosed method. In particular, lollipop oligomers, amplification target circles, address probes, detection probes, and strand displacement primers are useful components of such kits. Enzymes necessary for the disclosed method are also preferred components of such kits.

Method

The disclosed method makes use of a lollipop oligomer to provide sensitive and reliable detection and quantitation of target nucleic acid sequences. The disclosed method is particularly useful for in situ detection of nucleic acid sequences. The lollipop oligomers allow isothermic signal amplification through rolling circle amplification via a tail portion of the oligomer that becomes associated or topologically linked to the target nucleic acid sequence. The topological locking of the probe to the target is important for detection systems in which the amplified product may float away from the target. This may happen if the target sequence is extremely small or if the assay is being preformed on a substrate such as a metaphase chromosomes or any array that does not trap the tandem repeat DNA. By using multiple different primer (tail) sequences and corresponding DNA circles the method can be multiplexed, with the amplification product of each different circle being separately detectable. Lollipop oligomers can be circularized by chemical or enzymatic ligation. As used herein, the term ligation is not limited to enzymatic ligation of nucleic acid ends by ligase. Chemical coupling or other enzymatic coupling of the end of target probe portions (and gap oligonucleotides, if used) is also encompassed by this term. Lollipop oligomers hybridized to a target sequence and having ligated ends are referred to as locked lollipop oligomers.

The disclosed method is useful for detection, quantitation, and/or location of any desired nucleic acid sequences. The disclosed method can be multiplexed to detect numerous different nucleic acid sequences simultaneously or in a single assay. Thus, the disclosed method is useful for detecting, assessing, quantitating, profiling, and/or cataloging RNA expression in nucleic acid samples. The disclosed method is also particularly useful for detecting and discriminating single nucleotide differences in nucleic acid sequences. This specificity is possible due to the sensitivity of ligation to base mismatches around the ends of the oligomer arms. Thus, the disclosed is useful for detecting, assessing, quantitating, and/or cataloging single nucleotide polymorphisms, and other sequence differences between nucleic acids, nucleic acid samples, and sources of nucleic acid samples. In particular, the ratio of different polymorphs of a nucleic acid sequence in sample can be assessed due to the ability of the disclosed method to detect single copies of target sequences.

The disclosed method is applicable to numerous areas including, but not limited to, disease detection, mutation detection, RNA expression profiling, gene discovery, gene mapping (molecular haplotyping), agricultural research, and virus detection. Preferred uses include SNP detection in situ in cells, on microarrays, on DNA fibers, and on genomic DNA arrays; detection of RNA in cells; RNA expression profiling; molecular haplotyping; mutation detection; abnormal RNA (for example, overexpression of an oncogene or absence of expression of a tumor suppressor gene); expression in cancer cells; detection of viral genome in cells; viral RNA expression; detection of inherited diseases such as cystic fibrosis, muscular dystrophy, diabetes, hemophilia, sickle cell anemia; assessment of predisposition for cancers such as prostate cancer, breast cancer, lung cancer, colon cancer, ovarian cancer, testicular cancer, pancreatic cancer.

In a preferred form, the disclosed method involves mixing one or more different lollipop oligomers with one or more target samples and incubating under conditions that promote hybridization between the oligomers and target sequences in the samples. The arms of the lollipop oligomer are joined by ligation. The oligomers are also mixed with one or more amplification target circles and incubated under conditions that promote hybridization between the amplification target circles and the rolling circle replication primer portions of the oligomers. Mixing of the oligomers with the target samples and with the amplification target circles can be done simultaneously or in any order. For example, the amplification target circles can be mixed and hybridized to the oligomers prior to mixing with the target samples. It is preferred that the lollipop oligomers be mixed with the target samples and ligated prior to mixing with the amplification target circles.

To amplify the signal, DNA polymerase is mixed with the oligomers and amplification target circles and incubated under conditions that promote replication of the amplification target circles. Replication of the amplification target circle results in the formation of a long DNA strand containing numerous tandem repeats of the amplification target circle sequence (the DNA is referred to as tandem sequence DNA). Unique identification of multiple nucleic acid sequences in a single assay is accomplished by associating unique tail sequences (part of the oligomer) with each the various nucleic acid sequences to be detected. Each tail sequence (acting as a rolling circle replication primer) hybridizes to, and primes replication of, a unique amplification target circle. Detection of the unique sequences of the various resulting tandem sequence DNAs (each derived from a different, nucleic acid sequence-specific amplification target circle) indicates the presence in the nucleic acid sample of the target sequence corresponding to that tandem DNA sequence.

For multiplex forms of the method (that is, forms where multiple target sequences are detected in the same assay, a plurality of different lollipop oligomers are mixed with at least one target sample. Preferably, the target probe portions of each different oligomer are complementary to different target sequences and the rolling circle replication primers of each different oligomer are complementary to different amplification target circles. Alternatively, the rolling circle replication primers of at least two different oligomers can be complementary to the same amplification target circle.

Different target nucleic acid sequences need not be detected using a unique tail sequence for each target sequence. That is, the sequence of the tail portion (and in particular, the rolling circle replication primer portion of the tail portion) can be the same for groups of lollipop oligomers targeted to different sequences. Such matching sequences will prime replication of the same amplification target circle. This will result in a single form of tandem sequence DNA produced when any of the group of target sequences are present. This is useful, for example, to detect any one (or more) of a set of mutations in a gene. For example, some oncogenes can have numerous different mutations that are cancer-associated, and it would be useful to streamline detection of any one of them. Where multiple target sequences are associated with the same tail sequences, the target probe portion sequences will, of course, be unique for each target sequence (with the optional exception of oligomers using gap oligonucleotides or a gap-filling operation, discussed below).

In this form of the method, a plurality of different target samples each can be mixed with at least one type of lollipop oligomer. Preferably, the rolling circle replication primers of the oligomers mixed with different target samples are complementary to different amplification target circles. Two or more of the target samples can be mixed together after the oligomers have been added. In one embodiment of this form of the method, the set of oligomers mixed with each different target sample can be complementary to the same set of target sequences.

The same target sequence can also be targeted by multiple lollipop oligomers. That is, different oligomers having different tail sequences can be targeted to the same nucleic acid sequence. This is useful, for example, for detection of the same sequence in multiple samples in a single assay. For this, each different sample can be mixed with a different lollipop oligomer. This will associate a different tail sequence with the target sequence based on the source of the target sequence (that is, based on which sample the target sequence came from). The result will be a unique tandem sequence DNA (via a unique amplification target circle) for the target sequence from each source. In this way, the source of each target sequence can be determined even after the target samples are mixed together. Such mixing simplifies the manipulations needed for this type of assay.

The tail sequence of lollipop oligomers can also be detected and/or amplified using other techniques. For example, the tail sequence of the oligomer can be detected in any manner that nucleic acid sequence can be detected. Preferably, the tail sequence is amplified using some nucleic acid amplification technique such as PCR.

One form of the disclosed method uses lollipop oligomers that can form intramolecular associations to reduce the chance of background signal amplification. The intramolecular association is designed to keep the tail portion (or at least the rolling circle replication portion) inaccessible to an amplification target circle unless the oligomer is hybridized to a target sequence. This can be accomplished, for example, by having one or both of the arm portions associate with the tail portion. For example, the tail portion can be designed to be complementary to all or a portion of the right backbone portion, all or a portion of the left backbone portion, or a portion of the right backbone portion and a portion of the left backbone portion. Hybridization of the tail portion to either or both of the backbone portions will make the tail portion inaccessible to the amplification target circle. The backbone portions and the tail portion can also be designed to form a triple helix, which also makes the tail portion inaccessible to the amplification target circle. Hybridization of the target probe portions to the target sequence will free up the tail portion for hybridization to the amplification target circle. On the other hand, the tail and arms of oligomers that fail to associate with a target sequence will re-associate, thus making it inaccessible to amplification target circles. As a result, the non-hybridized oligomer will not produce tandem sequence DNA.

The ends of the oligomer arms are preferably linked by mixing ligase with the mixed oligomers and target samples, and incubating under conditions that promote ligation of the oligomers to form locked lollipop oligomers. Locked lollipop oligomers are lollipop oligomers hybridized to a target sequence and having ligated ends. In one form, the right arm portion has a free 5' end, the left arm portion has a free 3' end, and the end of the right arm portion is ligated to the end of the left arm portion to form the locked lollipop oligomer.

The oligomer arm ends are preferably directly linked, but can also be indirectly linked. In this latter case, at least one target sequence has a central region located between the 5' region and the 3' region and neither the left target probe portion nor the right target probe portion is complementary to the central region of the target sequence. Hybridization of the target probe portions to the target sequence leave the central region of the target single stranded. This gap sequence can be filled by hybridization of a gap oligonucleotide, gap-filling DNA synthesis, or a combination. Each gap oligonucleotide is complementary all or a portion of the central region of the target sequence.

The method is particularly useful for detecting single nucleotide differences between sequences. Some sequences are polymorphic. As used herein, a polymorphic sequence is a sequence that has different forms (i.e. differs in sequence) in different sources of the sequence. For example, one individual may have a gene having an A at a certain position and another individual may have a C at the same position in the same gene. These genes thus have a polymorphic sequence. The A and the C in these genes are polymorphic nucleotides. A polymorphic nucleotide is a nucleotide that differs between at least two forms of a polymorphic sequence. Put another way, the nucleotide position of the A and C is a polymorphic nucleotide position.

The disclosed method can be used to distinguish between these two forms of the gene based on this single difference. This can be accomplished, for example, by designing the lollipop oligomers so that the nucleotide at the end of the right target probe portion, the left target probe portion, or both are complementary to the polymorphic nucleotide in the target sequence. One oligomer would be designed to be fully complementary to the "A" form of the sequence (with a terminal T in one of the target probe portions) and the other would be designed to be fully complementary to the "C" form of the sequence (with a terminal G in one of the target probe portions). Since effective ligation of the ends requires that the terminal nucleotides be base paired to complementary nucleotides, the two oligomers will be effectively ligated only in the presence of the corresponding form of the target sequence. Similar effects can be achieved with the use of gap oligonucleotides. In this case, only a single lollipop oligomer would be needed since the gap oligonucleotides can be made specific for the different sequences.

EXAMPLE

This example illustrates use of the disclosed method to detect single nucleotide polymorphisms (SNPs). Detection of SNPs on interphase nuclei is not always successful. Lollipop oligomers provide a better platform for RCA-based detection of SNPs in cytological samples than prior techniques. The signal amplification by linear RCA will increase the sensitivity of allele discrimination by several orders of magnitude.

SNP Detection in Interphase Nuclei.

As an example, G542X allele of CFTR gene was used as the target for allele discrimination. Subsequent to the synthesis of open lollipop oligomers and the locked lollipop oligomers, the ability of the tail portion of a lollipop oligomer to serve as the primer for RCA applications was confirmed. The disclosed method was further demonstrated by in situ detection of homozygous and heterozygous CFTR loci in methanol: acetic acid fixed-interphase nuclei. To simultaneously differentiate between the two alleles, the respective lollipop oligomers (G542X WT lollipop oligomer and G542X WT lollipop oligomer) were constructed with tail portions designed to act as a rolling circle replication primer for either Circle-1 (SEQ ID NO:1) or Circle-3.1 (SEQ ID NO:2). Their detection, following RCA, was achieved with specific detection probes. G542X WT lollipop oligomer is formed from G542X WT lollipop arms (SEQ ID NO:3) and G542X WT lollipop tail (SEQ ID NO:4). G542X WT lollipop oligomer is formed from G542X MUT lollipop arms (SEQ ID NO:5) and G542X MUT lollipop tail (SEQ ID NO:6). G542X WT lollipop tail contains a rolling circle replication primer for circle 3.1. G542X MUT lollipop tail contains a rolling circle replication primer for circle 1.

Circle 1 (SEQ ID NO:1)
CGCATGTCCTATCCTCAGCTGTGATCAT-CAGAACTCACCTGTTAGACGCCAC CAGCTC-CAACTGTGAAGATCGCTTAT Circle 3.1 (SEQ ID NO:2)
GTGGAACGTGTAATGTTCATGATGAAAT-GTATCCTTGACAGCCGATGAGGT CCGTATCCT-TGACAGCCGATGAGGCAC G542X WT lollipop arms (SEQ ID NO:3):
5'-pAAGAACTATATTGTCTTTCTGAGCGGATA ACAAGA-(Allylamino-dU)-CACACAGGA TACAG-TATGACATGATTACGATGATTCCACCT TCTCC-3'

G542X WT lollipop tail containing primer for circle 3.1 (SEQ ID NO:4)
5'-C6-S-S-C6-AAAAAAAAAAAAAAAAAAAAAAAA (C18) CGTCATCA TGAACATTACACGTTCCAC-3'

G542X MUT lollipop arms (SEQ ID NO:5):
5'-pAAGA ACTATATTGTCTTTCTGAGCGGATAACAAGA-(Allylamino-dU)-CACACAGGATACAGTATGA CATGATTACGGTGATTCCACCTTCTCA-3'

G542X MUT lollipop tail containing primer for circle 1 (SEQ ID NO:6):
5'-C6-S-S-C6-AAAAAAAAAAAAAAACATGTTGTTACA-CAGCTGAGG ATAGGACAT-3'

1. Synthesis of open lollipop probes. Two oligonucleotides were synthesized. One for forming the right and left arm portions that hybridize to the target (padlock oligonucleotide) and other as the tail portion that serves as the rolling circle replication primer (primer oligonucleotide). Essentially the allyl-amino side chain in the backbone of the first oligonucleotide was activated by reacting with Sulfo-GMBS and the primer (tail) oligonucleotide containing a SH group at its 5' end was generated by the treatment of S-S oligonucleotide with the dithiothreitol (DTT). The arm portions with activated allyl-amino group and the tail oligonucleotide with the freshly generated SH group were reacted together to provide open lollipop oligomer that was purified by preparative poly-acrylamide gel electrophoresis (PAGE).

150 µl aqueous solution of S-S primer oligonucleotide (7.5 nmoles) was treated with 8 mg DTT and 5 µl of triethyl amine for 30 minutes. The oligonucleotide with a free 5' SH group was purified by passing the reaction mixture through a PD-10 column (Amesham Pharmacia Biotech). The purified oligonucleotide was freeze dried for further use. 40 µl of allyl amino oligonucleotide was mixed with 1 mg N-[gamma-maleimidobutyryloxy] sulfosuccinimide ester in 100 ml reaction buffer (50 mM Phosphate buffer, pH 7.0, 150 mM NaCl and 1 mM EDTA) for 1 hour at 37° C. The activated allylamino oligonucleotide was purified on a PD-10 column and concentrated by a Centricon concentrator. This concentrated oligonucleotide was reacted with the freeze dried SH oligonucleotide for 1 hour at 37° C. The lollipop oligomer, the slowest migrating oligonucleotide band, was purified on a 8% PAGE.

2. Formation of locked lollipop oligomers over target DNA. The open lollipop oligomers were end-labeled with [$^{32}$P] by the exchange reaction with T4 polynucleotide kinase and [$^{32}$P]ATP. Locked lollipop oligomers were formed over G542X target oligonucleotide by slowly annealing with a suitable open lollipop probe followed by their circularization with 5 units of Ampligase at 55° C. The efficiency of locked lollipop formation was evaluated by PAGE and autoradiography.

3. In-solution linear RCA of circles with lollipops. To determine whether the lollipop tail would function as a primer for the RCA signal amplification, linear RCA of Circle 3.1 was carried out with G542X-Wt-lollipop as the primer. The RCA amplification was evaluated by [$^{32}$P]dCTP incorporation.

Figure 4:
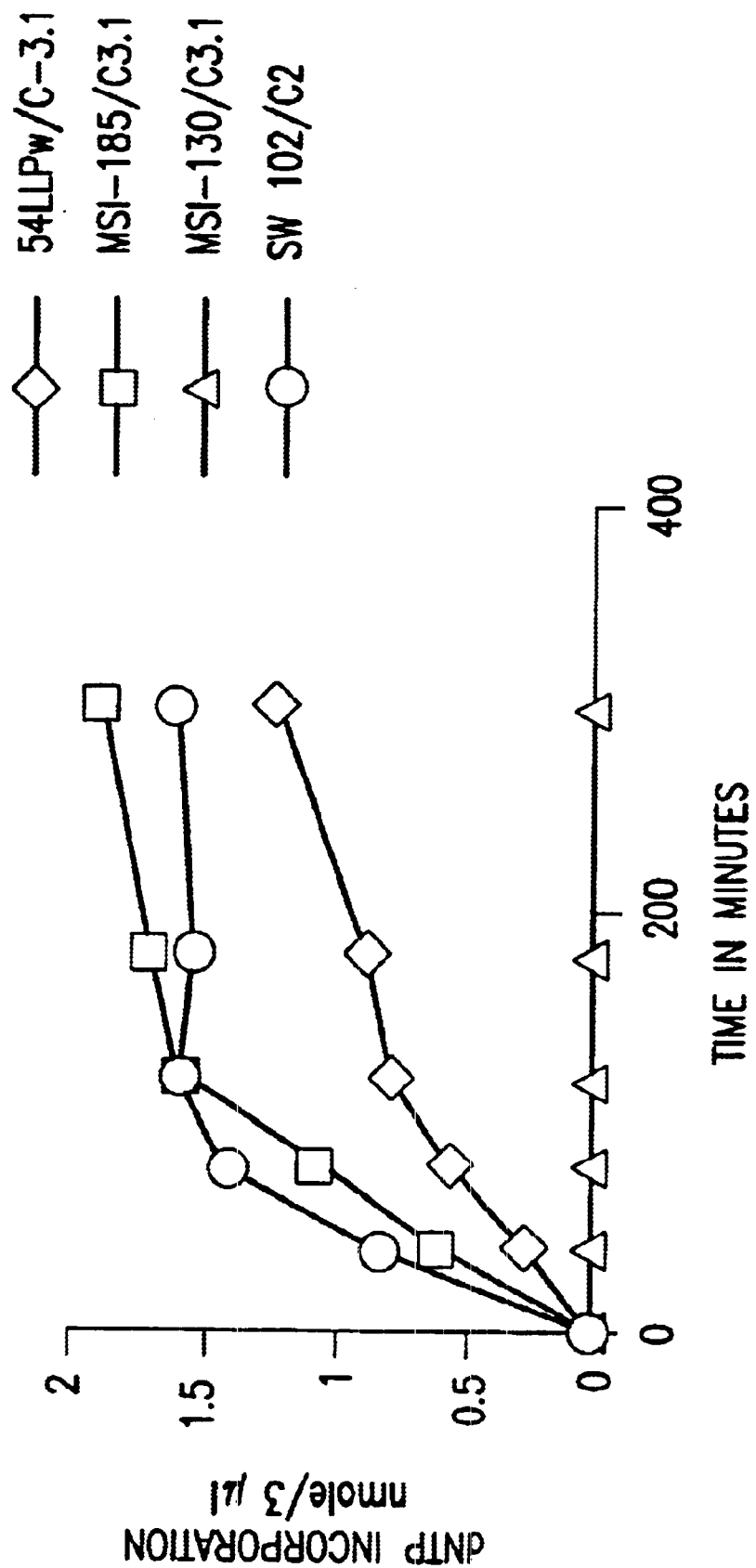
FIG. 4 is a graph of dNTP incorporation (in nmoles/3 $\mu$l) versus time (in minutes).
Figure 5:
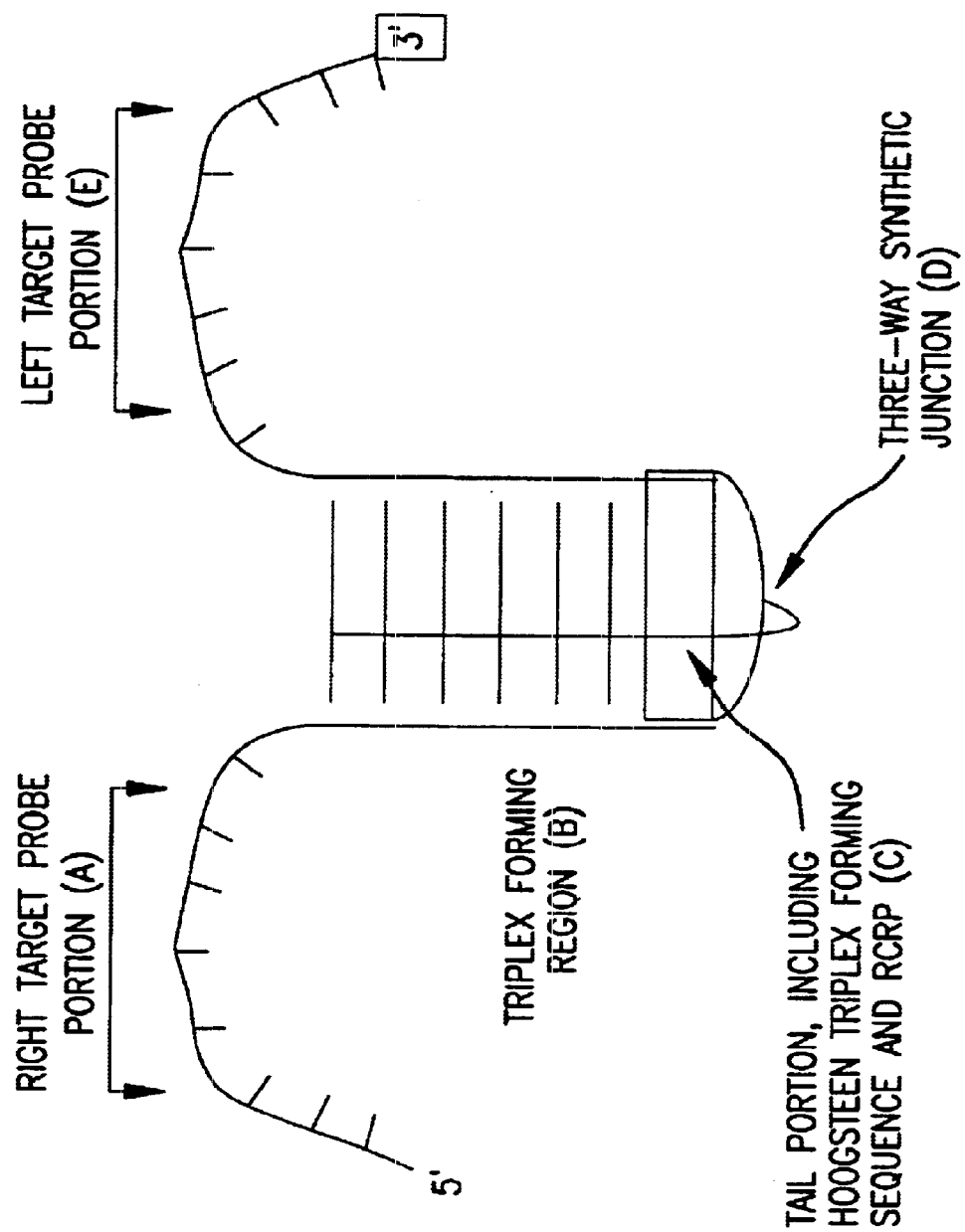
FIG. 5 is a diagram of an example of a lollipop oligomer that forms a triple helix involving the tail portion (containing a rolling circle replication primer sequence) and part of both arms. The target probe portions are not involved in the triple helix and are available for hybridization to the target sequence.
Figure 6:
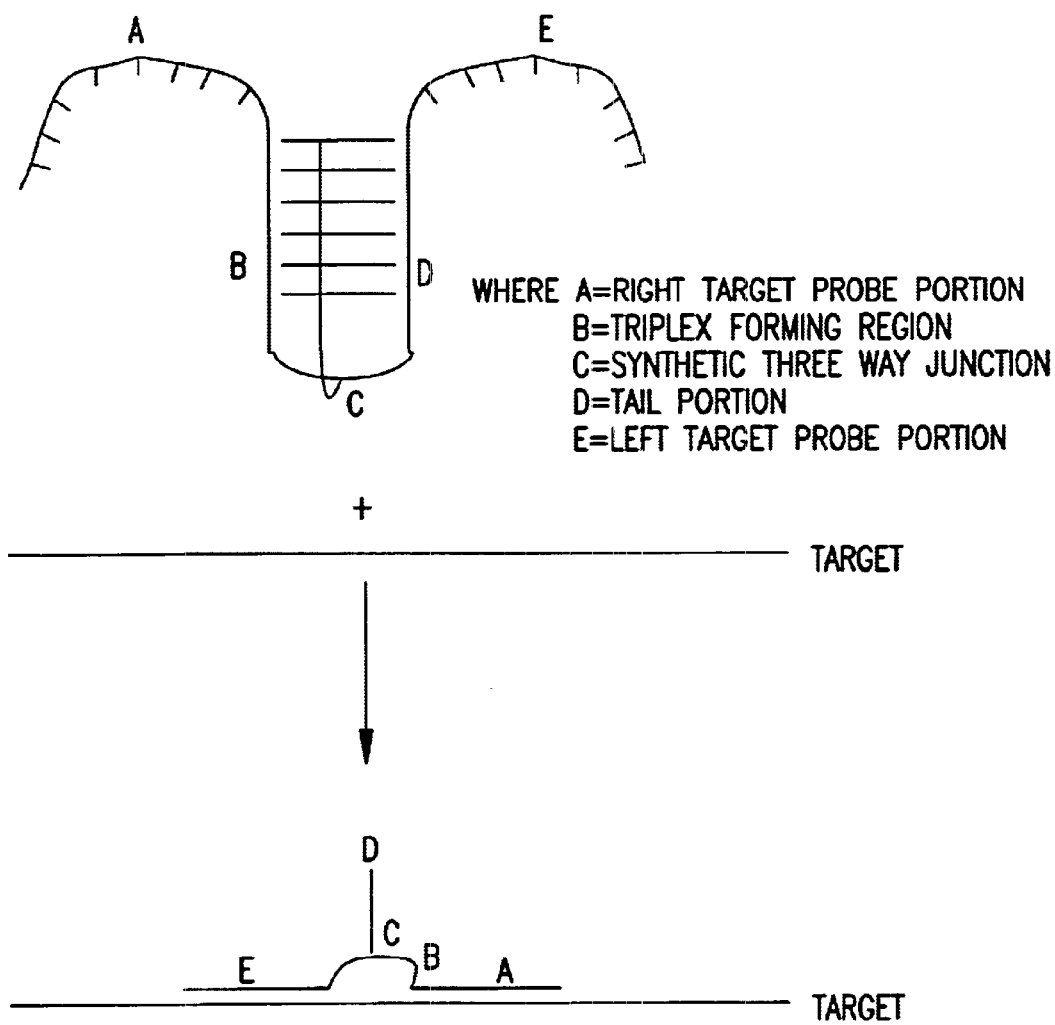
FIG. 6 is a diagram of how the tail portion of the lollipop oligomer shown in FIG. 5 becomes available for hybridization once the target probe portions hybridize to the target sequence.
Figure 7:
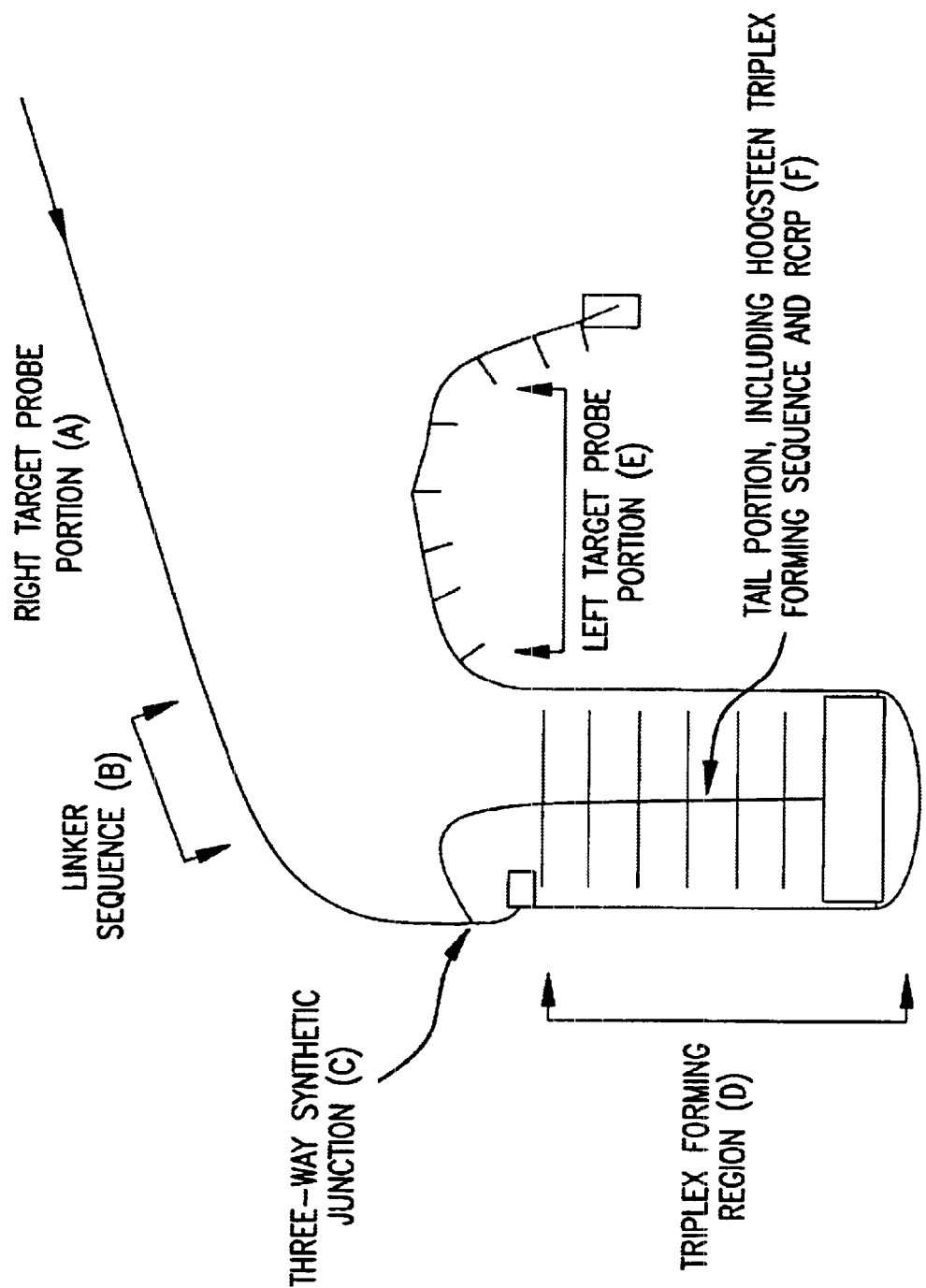
FIG. 7 is a diagram of an example of a lollipop oligomer that forms a triple helix involving the tail portion (containing a rolling circle replication primer sequence) and part of one of arms. This arm provides two of the strands involved in the triple helix. The target probe portions are not involved in the triple helix and are available for hybridization to the target sequence.
Figure 8:
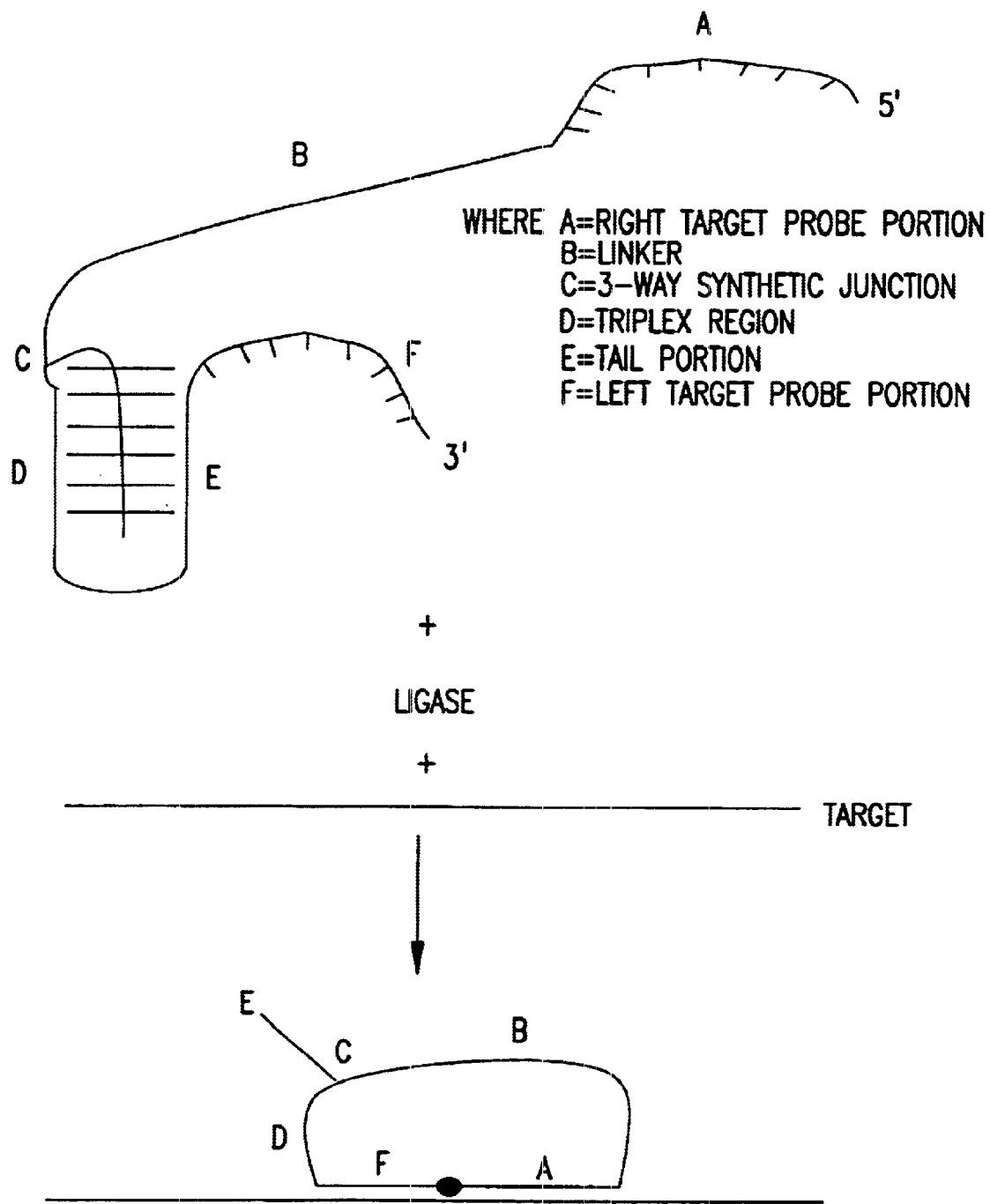
FIG. 8 is a diagram of how the tail portion of the lollipop oligomer shown in FIG. 7 becomes available for hybridization once the target probe portions hybridize to the target sequence.

First the primers (10 pmole) and the Circles (0.5 pmole) were annealed in a 6 µl reaction mixture (40 mM NaCl, 20 mM Tris/HCl pH7.0) for 30 minutes at room temperature. The linear RCA reaction was carried out at 37° C. by adding the annealed circle-primer mixture to 14 µl of linear RCA cocktail (1 mM each dATP, dGTP, TTP, dCTP, 1×φ29 polymerase buffer [50 mM Tris/HCL pH 7.4, 10 mM MgCl$_2$, 100 µg/ml bovine serum albumin (BSA)], 0.2 µl [$^{32}$P] dCTP and 1 µl 100 29 DNA polymerase). 3 µl of the linear RCA reaction mixture was removed at different time points to evaluate the incorporation of $^{32}$P dCTP. The results are shown in FIG. 4. SW 102/C2 is a positive control for the RCA reaction using a known small circle and cognate primer. MSI-130/C3.1 is the lollipop without the tail (primer) showing no RCA in the presence of circle 3.1. MSI-185/C3.1 is the complete lollipop before ligation showing robust RCA in the presence of circle 3.1. 54LLPw/C3.1 is the lollipop after ligation showing the it can still prime RCA using circle 3.1.

4. Detection of G542X locus by lollipops in interphase nuclei. Slides with methanol: acetic acid-fixed interphase lymphocyte nuclei were incubated at 55° C. for 30 minutes. Slides were dipped in a solution containing 70% formamide, and 2×SSC (1×SSC is 0.15 M NaCl, 0.015 M Na Citrate) at 70° C. for 75 seconds and passed through a series of ice cold 70%, 90% and 100% ethanol solutions to denature the nuclei. 40 µl of ligation mixture containing 10 nM lollipop, 4 µg BSA, 1×ampligase buffer (20 mM Tris/HCL pH 8.3, 25 mM KCl, 10 mM MgCl$_2$, 0.5 mM NAD, 0.01% Triton X-100) and 5 units of Ampligase was applied on each slide and incubated at 55° C. for 2 hours. Slides were washed three times for 5 minutes with 2×SSC, 0.1% Tween 20 at 42° C. 40 µl of RCA reaction mixture (20 nM circle 3.1, 0.4 mM each dATP, dGTP, TTP, dCTP, 4 µg BSA, 1×φ29 buffer and 200 ng φ29 DNA polymerase) was placed on these slides and incubated for 30 minutes at 37° C. Slides were washed three times for 5 minutes in 2×SSC, 0.1% Tween 20 at 42° C. 50 µl of detection solution (1 µM Cy3-detection probes [SEQ ID NO:7, SEQ ID NO: 8, SEQ ID NO:9 ], 2×SSC, 1% BSA and 0.1% Tween 20) was applied to each slide and incubated for 30 minutes at 37° C. Slides were again washed three times with 2×SSC, 0.1 % Tween 20 at 42° C., stained with DAPI and used for imaging.

Detection Probe A for Circle 1 (SEQ ID NO:7)
TCAGAACTCACCTGTTAG

Detection Probe B for Circle 1 (SEQ ID NO:8)
ACTGTGAAGATCGCTTAT

Detection Probe for Circle 3.1 (SEQ ID NO:9)
GCATCCTTGACAGCCGATGAGGCTG

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. A method of amplifying nucleic acid sequences, the method comprising
    (a) mixing one or more different lollipop oligomers with one or more target samples each comprising one or more target sequences, and incubating under conditions that promote hybridization between the oligomers and the target sequences,
    wherein the lollipop oligomers each comprise a branched oligomer comprising a tail portion, wherein the tail portion comprises a rolling circle replication primer, wherein the rolling circle replication primer comprises a complementary portion that is complementary to a primer complement portion of an amplification target circle,
    (b) prior to, simultaneous with, or following step (a), mixing one or more amplification target circles with the oligomers, and incubating under conditions that promote hybridization between the amplification target circles and the rolling circle replication primer portions of the oligomers, and
    (c) mixing DNA polymerase with the oligomers and amplification target circles, and incubating under conditions that promote replication of the amplification target circles,
    wherein replication of the amplification target circles results in the formation of tandem sequence DNA.

2. The method of claim 1 wherein at least one of the lollipop oligomers further comprises a right arm portion and a left arm portion, wherein the right arm portion and the left arm portion are coupled together, wherein the tail portion is coupled to the oligomer at the junction of the right arm portion and the left arm portion, wherein the right arm portion of at least one of the oligomers comprises a right target probe portion and a right backbone portion, wherein the left arm portion comprises a left target probe portion and a left backbone portion, wherein the right target probe portion is at the end of the right arm portion, wherein the left target probe portion is at the end of the left arm portion, wherein the target probe portions are complementary to at least one of the target sequences, wherein the target sequence comprises a 5' region and a 3' region, wherein the left target probe portion and the right target probe portion of the oligomer are each complementary to the 3' region and the 5' region, respectively, of the target sequence.

3. The method of claim 2 further comprising, simultaneous with, or following step (a), mixing ligase with the oligomers and target samples, and incubating under conditions that promote ligation of the oligomers to form locked lollipop oligomers.

4. The method of claim 3 wherein the right arm portion has a free 5' end, and the left arm portion has a free 3' end, wherein the end of the right arm portion is ligated to the end of the left arm portion to form the locked lollipop oligomer.

5. The method of claim 3 wherein the right arm portion has a free 5' end, and the left arm portion has a free 3' end, wherein the at least one target sequence further comprises a central region located between the 5' region and the 3' region, wherein neither the left target probe portion nor the right target probe portion is complementary to the central region of the target sequence, wherein step (a) further comprises mixing one or more gap oligonucleotides with at least one of the target samples, wherein each gap oligonucleotide is complementary all or a portion of the central region of the target sequence.

6. The method of claim 3 wherein the right arm portion has a free 5' end, and the left arm portion has a free 3' end, wherein the at least one target sequence further comprises a central region located between the 5' region and the 3' region, wherein neither the left target probe portion nor the right target probe portion is complementary to the central region of the target sequence, wherein the method further comprises, prior to, or simultaneous with, mixing ligase with the lollipop oligomers and target samples, mixing gap-filling DNA polymerase with the lollipop oligomers and target samples.

7. The method of claim 3 wherein the right arm portion has a free 5' end, and the left arm portion has a free 3' end, wherein the at least one target sequence further comprises a central region located between the 5' region and the 3' region, wherein neither the left target probe portion nor the right target probe portion is complementary to the central region of the target sequence, wherein step (a) further comprises mixing one or more gap oligonucleotides with at least one of the target samples, wherein each gap oligonucleotide is complementary all or a portion of the central region of the target sequence, wherein the method further comprises, prior to, or simultaneous with, mixing ligase with the lollipop oligomers and target samples, mixing gap-filling DNA polymerase with the lollipop oligomers and target samples.

8. The method of claim 3 wherein the ligase is selected from the group consisting of AMPLIGASE®, T4 DNA ligase, T4 RNA ligase, *E. coli* DNA ligase, Taq DNA ligase, Thermus thermophilus DNA ligase, Thermus scotoductus DNA ligase, and Rhodothermus marinus DNA ligase.

9. The method of claim 2 wherein the right target probe portion and the left target probe portion comprise peptide nucleic acids.

10. The method of claim 2 wherein the tail portion is complementary to all or a portion of the right backbone portion, all or a portion of the left backbone portion, or a portion of the right backbone portion and a portion of the left backbone portion.

11. The method of claim 2 wherein the tail portion, the right backbone portion, and the left backbone portion can form a triple helix.

12. The method of claim 2 wherein the tail portion, right arm portion, and left arm portion are oligonucleotides.

13. The method of claim 2 wherein at least a portion of the tail portion, right arm portion, or left arm portion is a linker.

14. The method of claim 2 wherein the target sequence corresponds to one form of a polymorphic sequence.

15. The method of claim 14 wherein the nucleotide at the end of the right target probe portion, the left target probe portion, or both are complementary to a polymorphic nucleotide in the target sequence.

16. The method of claim 2 wherein a plurality of different lollipop oligomers are mixed with at least one target sample, wherein the target probe portions of each different oligomer are complementary to different target sequences.

17. The method of claim 16 wherein the rolling circle replication primers of each different oligomer are complementary to different amplification target circles.

18. The method of claim 16 wherein the rolling circle replication primers of at least two different oligomers are complementary to the same amplification target circle.

19. The method of claim 2 wherein a plurality of different target samples are each mixed with at least one of the lollipop oligomers.

20. The method of claim 19 wherein the rolling circle replication primers of the oligomers mixed with different target samples are complementary to different amplification target circles.

21. The method of claim 20 further comprising following step (a) and prior to, simultaneous with, or following step (b), mixing two or more of the target samples.

22. The method of claim 20 wherein the set of oligomers mixed with each different target sample are complementary to the same set of target sequences.

23. The method of claim 1 wherein the DNA polymerase is selected from the group consisting of bacteriophage φ29 DNA polymerase, phage M2 DNA polymerase, phage φ PRD1 DNA polymerase, VENT® DNA polymerase, Klenow fragment of *E. coli* DNA polymerase I, T5 DNA polymerase, PRD 1 DNA polymerase, T7 DNA polymerase, T7 Sequenase™, ΔTts Polymerase, and T4 DNA polymerase holoenzyme.

24. The method of claim 1 wherein at least one of the target sequences is associated with a disease selected from the group consisting of inherited diseases, cystic fibrosis, muscular dystrophy, diabetes, hemophilia, sickle cell anemia, cancers, prostate cancer, breast cancer, lung cancer, colon cancer, ovarian cancer, testicular cancer, and pancreatic cancer.

25. The method of claim 1 detection of at least one of the target sequences is used for disease detection, mutation detection, RNA expression profiling, gene discovery, gene mapping, molecular haplotyping, virus detection, single nucleotide polymorphism detection, detection of RNA in cells, detection of abnormal RNA, detection of overexpression of an oncogene, detection of the absence of expression of a tumor suppressor gene, detection of expression in cancer cells, detection of viral genomes in cells, detection of viral RNA expression, detection of inherited diseases, detection of cystic fibrosis, detection of muscular dystrophy, detection of diabetes, detection of hemophilia, detection of sickle cell anemia, assessment of predisposition for cancer, assessment of predisposition for prostate cancer, assessment of predisposition for breast cancer, assessment of predisposition for lung cancer, assessment of predisposition for colon cancer, assessment of predisposition for ovarian cancer, assessment of predisposition for testicular cancer, assessment of predisposition for pancreatic cancer, or a combination.

26. The method of claim 1 wherein at least one of the target sequences is detected in situ in cells, on microarrays, on DNA fibers, or on genomic DNA arrays.

27. A method of detecting target nucleic acid sequences, the method comprising
 (a) mixing one or more different lollipop oligomers with one or more target samples each comprising one or more target sequences, and incubating under conditions that promote hybridization between the oligomers and the target sequences,
 wherein the lollipop oligomers each comprise a branched oligomer comprising a tail portion, a right arm portion, and a left arm portion, wherein the right arm portion and the left arm portion are coupled together, wherein the tail portion is coupled to the oligomer at the junction of the right arm portion and the left arm portion, wherein the tail portion comprises an address tag,
 wherein the right arm portion of at least one of the oligomers comprises a right target probe portion and a right backbone portion, wherein the left arm portion comprises a left target probe portion and a left backbone portion, wherein the right target probe portion is at the end of the right arm portion, wherein the left target probe portion is at the end of the left arm portion,
 wherein the target probe portions are complementary to at least one of the target sequences, wherein the target sequence comprises a 5' region and a 3' region, wherein the left target probe portion and the right target probe portion of the oligomer are each complementary to the 3' region and the 5' region, respectively, of the target sequence,
 (b) detecting the address tags.

28. The method of claim 27 wherein the address tags are detected by hybridization.

29. A method of amplifying nucleic acid sequences, the method comprising
 replicating one or more amplification target circles, wherein replication of the amplification target circles results in the formation of tandem sequence DNA,
 wherein the amplification target circles are mixed with one or more different lollipop oligomers, wherein the lollipop oligomers each comprise a branched oligomer comprising a tail portion, wherein the tail portion comprises a rolling circle replication primer, wherein the rolling circle replication primer comprises a complementary portion that is complementary to a primer complement portion of at least one of the amplification target circles, wherein the rolling circle replication primer primes replication of the amplification target circle, wherein at least one of the lollipop oligomers is hybridized to a target sequence in a target sample.

30. The method of claim 29 wherein at least one of the lollipop oligomers hybridized to a target sequence in a target sample is ligated to form a locked lollipop oligomer.

* * * * *

UNITED STATES PATENT AND TRADEMARK OFFICE
CERTIFICATE OF CORRECTION

PATENT NO.    : 6,686,157 B2
DATED         : February 3, 2004
INVENTOR(S)   : Ward et al.

It is certified that error appears in the above-identified patent and that said Letters Patent is hereby corrected as shown below:

<u>Title page,</u>
Item [73], Assignee, change "Molecular Staging Inc., New Haven, CT (US)" to read -- Molecular Staging Inc., New Haven, CT (US); Yale University, New Haven, CT (US) --.

Signed and Sealed this

Eighteenth Day of May, 2004

JON W. DUDAS
*Acting Director of the United States Patent and Trademark Office*